(12) United States Patent
Jurinke et al.

(10) Patent No.: US 6,303,309 B1
(45) Date of Patent: *Oct. 16, 2001

(54) METHOD FOR DISSOCIATING BIOTIN COMPLEXES

(75) Inventors: Christian Jurinke, Hamburg; Dirk Van den Boom, Dreieich, both of (DE); Hubert Köster, Concord, MA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/337,388

(22) Filed: Jun. 21, 1999

Related U.S. Application Data

(63) Continuation of application No. 08/649,876, filed on May 13, 1996, now Pat. No. 6,022,688.

(51) Int. Cl.[7] ............................. C12Q 1/68; C07H 21/00; C07K 16/44

(52) U.S. Cl. ................................ 435/6; 435/7.1; 435/7.2; 435/501; 536/25.3; 530/300; 530/350; 530/387.1

(58) Field of Search ................................... 435/6, 7.1, 7.2, 435/501; 536/25.3; 530/300, 350, 387.1

(56) References Cited

U.S. PATENT DOCUMENTS

| | | | |
|---|---|---|---|
| 4,282,287 | 8/1981 | Giese | 428/407 |
| 4,762,881 | 8/1988 | Kauer | 525/54.11 |
| 5,283,342 | 2/1994 | Gustavson et al. | 548/304.1 |
| 5,451,683 | 9/1995 | Barrett et al. | 548/302.7 |
| 5,484,701 | 1/1996 | Cocuzza et al. | 435/6 |
| 5,527,675 | 6/1996 | Coull et al. | 435/6 |
| 5,605,708 | 2/1997 | Koster et al. | 435/6 |
| 5,643,722 | 7/1997 | Rothschild | 435/6 |
| 5,900,481 | 5/1999 | Lough et al. | 536/55.3 |
| 5,928,906 | 7/1999 | Koster et al. | 435/91.2 |
| 6,022,688 | * 2/2000 | Jurinke et al. | 435/6 |
| 6,043,031 | 3/2000 | Koster et al. | 435/6 |
| 6,133,436 | 10/2000 | Koster et al. | 536/24.3 |

FOREIGN PATENT DOCUMENTS

| | | |
|---|---|---|
| 0456304 | 11/1991 | (EP) . |
| 0701001 | 3/1996 | (EP) . |
| 9416101 | 7/1994 | (WO) . |
| 9629431 | 9/1996 | (WO) . |
| 9637630 | 11/1996 | (WO) . |
| 97/43617 | * 11/1997 | (WO) . |
| 9820019 | 5/1998 | (WO) . |
| 9820020 | 5/1998 | (WO) . |
| 9820166 | 5/1998 | (WO) . |

OTHER PUBLICATIONS

Barany, F., *Proc. Natl. Acad. Sci.* 88:189–193 (1991).
Beck et al., Chemiluminescent detection of DNA: application for DNA sequencing and hybridization, *Nuc. Acids Res.* 17(13):5115–23 (1989).
Chilkoti et al., Molecular origins of the slow streptavidin–biotin dissociation kinetics, *J. Am. Chem. Soc.* 117(43):10622–10628 (1995).
Dynabeads, Dynal, Inc.
Finn et al., Ligands for insulin receptor isolation, *Biochemistry* 23(12):2554–2558 (1984).
Fujita et al., Surprising lability of biotin–streptavidin bond during transcription of biotinylated DNA bound to paramagnetic streptavidin beads, *Bio Techniques* 14(40:608–617 (1993).
Green, Michael N., Avidin, *Advances in Protein Chemistry* 29:85–133 (1975).
Green et al., The dissociation of avidin–biotin complexes by guanidinium chloride, *Biochem. J.* 130:707–711 (1972).
Hnatowich et al., *Int. J. Appl. Radiat. Isotop* 33:327 (1982).
Hornes et al., Magnetic DNA hybridization properties of oligonucleotide probes attached to superparamagnetic beads and their use in the isolation of Poly(A) mRNA from eukaryotic cells, *GATA* 7(6):145–150 (1990).
Hultman et al., Direct solid phase sequencing of genomic and plasmid DNA using magnetic beads as solid support, *Nucleic Acids Res.* 17(13):4937–4946 (1989).
Jurinke et al., Recovery of nucleic acids from immobilized biotin–streptavidin complexes using ammonium hydroxide and applications in MALDI–TOF mass spectrometry, *Anal Chem.* 69(5):904–10 (1997).
Jurinke et al., Analysis of ligase chain reaction products via matrix–assisted laser desorption/ionization time–of–flight mass spectrometry, *Anal. Biochemistry* 237:174–181 (1996).
Kan and Dozy, Antenatal diagnosis of sickle–cell anaemia by D.N.A. analysis of amniotic–fluid cells, *Lancet* 2:910–912 (1978).
Karas and Hillenkamp, Laser desorption ionization of proteins with molecular masses exceeding 10 000 daltons, *Anal Chem.* 60:2299–2301 (1988).
Gildea et al., A versatile acid–labile linker for modification of synthetic biomolecules, *Tetrahedron Lttrs* 31:7095 (1990).
Low et al., Sequence–specific binding of echinomycin to DNA: evidence for conformational changes affecting flanking sequences, *Nucleic Acids Res.* 12:4865–4879 (1984).
Mitchell et al., Advances in biomagnetic separation, Eaton Publishing, Natick, MA, USA, pp. 31–48 (1994).
Saiki et al., Enzymatic amplification of β–globin genomic sequences and restriction site analysis for diagnosis of sickle cell anemia, *Science* 230:1350–1355 (1985).
Stahl et al., Solid phase DNA sequencing using the biotin–avidin system, *Nucleic Acids Res.* 16(7):3025–3038 (1988).

(List continued on next page.)

*Primary Examiner*—Christopher S. F. Low
*Assistant Examiner*—Stephen Tu
(74) *Attorney, Agent, or Firm*—Stephanie L. Seidman; Heller Ehrman White & McAuliffe LLP

(57) ABSTRACT

A method for dissociating a complex of a biotin compound and a biotin-binding compound, by contacting the complex with an amine, is disclosed.

32 Claims, 8 Drawing Sheets

OTHER PUBLICATIONS

Tang et al., Matrix–assisted laser desorption/ionization of restriction enzym–digested DNA, *Rapid Comm. Mass. Spectrom.* 8:183–186 (1994).

Tang et al., Matrix–assisted laser desorption/ionization mass spectrometry of immobilized duplex DNA probes, *Nucleic Acids Res.* 23:3126–3131 (1995).

Tong et al., Solid–phase method for the purification of DNA sequencing reactions, *Anal. Chem.* 64:2672–2677 (1992).

van den Boom et al., Forward and reverse DNA sequencing in a single reaction, *Anal. Biochem.* 256(1):127–9 (1998).

van den Boom et al., Combined amplification and sequencing in a single reaction using two DNA polymerases with differential incorporation rates for dideoxynucleotides, *J. Biochem Biophys Methods* 35(2):69–79 (1997).

Orchin et al. (ed), The Vocabulary of Organic Chemistry, John Wiley & Sons, 1980, p. 87.

Duval, Dictionaire de la Chimie et de ses Applications, 3rd ed., 1978, p. 60.

Barton & Ollis, Comprehensive Organic Chemistry vol. 2, Pergamon Press, 1979, p. 4 and 26.

Bennet, Concise Chemical and Technical Dictionary, 3rd Ed., 1974, Chemical Publishing & Co., New York, p. 47, 48.

\* cited by examiner

Detection of PCR products and LCR products

Step 1 — PCR reaction carried out with biotinylated oligonucleotide

Step 2 — Ultrafiltration to remove non-extended primers. Immobilization on streptavidin-coated solid support Step 3 — Purification, treatment with ammonia Step 4 — Detection, or other downstream applications

```
                            SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:1:

AGCTCTATAT CGGGAAGCCT                                              20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

TTGCCTGAGT GCAGTATGGT                                              20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
```

(xi) SEQUENCE DESCRIPTION: SEQ ID NO:3:

AGCTCTATAT CGGGAAGCCT                                              20

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GTAAAACGAC GGCCAGT                                                 17

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

TTGCGTACAC ACTGGCCGTC GTTTTACAAC GTCGTGACTG GGAAAACCTC              50

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

GTAAAACGAC GGCCAGT                                                 17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

GAGATCTCCT AGGGGCC                                                 17

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

TACATTCCCA ACCGCGTGGC ACAAT                                        25

-continued (2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

CCAGTGGCAA GC                                              12

METHOD FOR DISSOCIATING BIOTIN COMPLEXES

This application is a continuation of U.S. application Ser. No. 08/649,876, filed May 13, 1996, now U.S. Pat. No. 6,022,688.

BACKGROUND OF THE INVENTION

Today many powerful techniques, derived from research in molecular biology, are ready to be used in routine diagnostic or forensic applications. Prominent examples are the polymerase chain reaction, PCR (Saiki, R. K. et al., *Science*, 230, 1350–1355), based on a cyclic, template-directed primer extension reaction; the analysis of restriction fragment length polymorphisms (Kan, Y. W. and A. M. Dozy, *Lancet*, 2, 910–912); and the ligase chain reaction (Barany, F. (1991) Proc. Natl. Acad. Sci. USA, 88, 189–193) to detect known point mutations at the ligation site of adjacent oligonucleotides.

It appears likely that in the near future, application of these techniques for analysis of DNA will augment or supplant conventional diagnostic procedures based, for example, on the detection of disease-associated metabolites.

Currently, the most common tool for the analysis of DNA is fragment separation by gel electrophoresis. However, in many cases, electrophoretic analysis and subsequent detection of labeled fragments is more time-consuming than performing the enzymatic reaction, and therefore is a time-limiting step.

Detection techniques are under development which will enhance signal acquisition and provide automated and parallel sample processing, and will likely lead to cost-efficient and time-saving sample processing in diagnostic and forensic applications. Also, large DNA sequencing projects, such as the Human Genome Initiative, that seek to sequence genes or entire genomes, for research or diagnostic purposes, require automated techniques with a high throughput to ensure timely completion of the project.

A promising tool which meets at least some of these criteria is the analysis of DNA fragments by matrix assisted laser desorption/ionisation time-of-flight (MALDI-TOF) mass spectrometry (Karas, M. and Hillenkamp, F. (1988) *Anal. Chem.*, 60, 2299–2301).

The biotin-streptavidin system is a common and useful tool for the purification of biotinylated materials (X. Tong and L. M. Smith (1992) *Anal. Chem.*, 64, 2672–2677), e.g., products from PCR or sequencing reactions. Streptavidin (and also avidin) are bacterial proteins which form tight complexes with biotin, including biotin conjugated to other molecules such as nucleic acids. The stability of the biotin-streptavidin complex during intensive washing permits removal of non-specifically bound and non-biotinylated material, which is of great importance for the success of reaction product analysis. The properties of the biotin-streptavidin complex can be used in systems employing biotin bound to streptavidin on a solid support and to yield immobilized biotinylated molecules. The solid phase, including the complexed biotinylated molecules, can be physically collected for further manipulations, including i) removal of excess reaction components like buffer salts, enzymes or deoxynucleotide triphosphates (dNTPs) or ii) performance of enzymatic reactions like nucleolytic digests and solid phase sequencing.

A broad spectrum of applications for the biotin-streptavidin system is known and even techniques not yet developed will be adaptable to this system (see, e.g., Stahl et al. *Nucleic Acids Research* (1988) 16, 3025–3038; Hultman et al. *Nucleic Acids Res.* (1989) 17, 4937–4946; Hornes et al. *Genet. Anal.* (1990) 7, 145–150).

Although the biotin-streptavidin complex is the result of non-covalent bonding, the affinity of streptavidin for biotin is about one million times more powerful than that of most antibody-antigen interactions. However, for the analysis of reaction products it is important to provide conditions for an effective dissociation of the complex while recovering the analyte molecules without modification.

Currently the recovery of biotinylated substances is based on biotin-streptavidin complex dissociation using substances like phenol, urea, or, most preferably 95% formamide at temperatures between 25 and 100° C. (Cocuzza et al., U.S. Pat. No. 5,484,701, 1996).

However, the use of formamide has been shown to be harmful for sample crystallization, a necessary process for MALDI-TOF analysis, and for various enzymatic reactions (e.g. reactions employing alkaline phosphatase). Therefore methods based on the use of formamide are only useful for subsequent gel electrophoretic analysis, but are harmful if enzymatic reactions should be performed involving the isolated material or other analytical tools are to be applied. The endo- or exonucleolytic digest, for example, of PCR products would benefit from a method allowing isolation of single-stranded PCR products which can be digested after purification.

Gel electrophoresis, the time and sample throughput-limiting factor in DNA diagnostics, will be replaced by more efficient techniques in the near future. These applications suggest that efficient methods linking the biotin-streptavidin technology to, for example, MALDI-TOF MS, are strongly required.

SUMMARY OF THE INVENTION

In one aspect, the invention provides a method for dissociating a complex comprising a biotin compound and a biotin-binding compound. The method includes contacting the complex with an effective amount of an amine, under conditions such that the complex is dissociated, thereby forming a biotin compound and a biotin-binding compound.

In preferred embodiments, the complex is contacted with an amine at a temperature of between about 25° C. and about 100° C. In preferred embodiments, the biotin compound is a biotinylated macromolecule. In preferred embodiments, the biotinylated macromolecule is selected from the group consisting of a biotinylated nucleic acid sequence, a biotinylated protein, a biotinylated carbohydrate, and a biotinylated lipid. In preferred embodiments, the biotin-binding compound is selected from the group consisting of avidin, streptavidin, and derivatives thereof.

In preferred embodiments, the biotin-binding compound is immobilized on a solid support. In preferred embodiments, the solid support is a magnetic bead.

In certain preferred embodiments, after the contacting step, the biotin compound is separated from the biotin-binding compound. In preferred embodiments, after the separation step, the biotin compound is purified. In preferred embodiments, the biotin compound is purified by a method selected from the group consisting of lyophilization, precipitation, filtration, and dialysis.

In preferred embodiments, prior to the contacting step, the complex is purified.

In other preferred embodiments, the biotin compound is immobilized on a solid support.

In preferred embodiments, after dissociation of the complex, at least one of the biotin compound and the biotin-binding compound is analyzed by mass spectrometry.

In certain preferred embodiments, after dissociation of the complex, the biotin-binding compound retains biotin-binding activity. In preferred embodiments, after dissociation of the complex, the biotin moiety of the biotin compound remains substantially intact.

In particularly preferred embodiments, the amine is ammonia. In other preferred embodiments, the amine is a primary amine.

In another aspect, the invention provides a method for analyzing a biotinylated nucleic acid. The method includes the steps of contacting the biotinylated nucleic acid with a biotin-binding compound, thereby forming a biotinylated nucleic acid:biotin-binding compound complex and contacting the complex with an effective amount of an amine, under conditions such that the complex is dissociated, thereby releasing a biotinylated nucleic acid and a biotin-binding compound; and analyzing the biotinylated nucleic acid.

In preferred embodiments, the nucleic acid is DNA. In preferred embodiments, the biotin-binding compound is immobilized. In preferred embodiments, the biotinylated nucleic acid is analyzed by mass spectrometry. In preferred embodiments, the amine is ammonia.

Thus, in one embodiment, the subject method provides a process for isolating biotinylated single-stranded or double-stranded DNA from enzymatic reactions for the purpose of purification and sample conditioning, which can be followed by subsequent analysis (e.g., by mass spectrometry) or further enzymatic reactions.

The above and further features and advantages of the instant invention will become clearer from the following detailed description and claims.

DETAILED DESCRIPTION OF THE INVENTION

Figure 1:
FIG. 1 is a schematic drawing of the purification of biotinylated PCR products where the reaction was carried out in solution.
Figure 1:
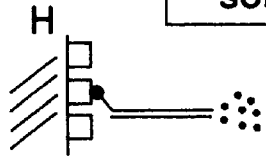
Figure 1:

In general, the invention features a method for dissociating biotin compounds, including biotin-conjugated (biotinylated) carbohydrates, proteins, polypeptides, peptides and nucleic acid molecules (e.g., double-stranded or single-stranded DNA or RNA), from biotin-binding compounds, including streptavidin or avidin compounds. Once isolated, the biotin compound (or biotin-binding compound) can be analyzed using various detection methods and/or employed in further enzymatic reactions.

The term "biotin compound", as used herein, refers to biotin and biotin derivatives and analogs. Thus, "biotin compounds" include compounds such as biotin, iminobiotin, and covalent or non-covalent adducts of biotin with other moieties. Preferred biotin compounds retain the ability to bind to avidin or streptavidin, or other biotin-binding compounds. For example, biotin has been used to derivatize a variety of molecules, including both small molecules (for example, chelating agents, e.g., $^{186}$Re-chelators conjugated to biotin, see, e.g., U.S. Pat. No. 5,283,342 to Gustavson et al.) as well as large molecules, including biomolecules (e.g., nucleic acids (including DNA, RNA, DNA/RNA chimeric molecules, nucleic acid analogs, and peptide nucleic acids), proteins (including enzymes and antibodies), carbohydrates, lipids, and the like). Methods of conjugating biotin to other molecules ("biotinylation") are well known in the art, and a variety of biotinylating reagents are commercially available (from, e.g., Pierce, Rockford, Ill.). A variety of coupling or crosslinking agents such as protein A, carbodiimide, dimaleimide, dithio-bis-nitrobenzoic acid (DTNB), N-succinimidyl-S-acetyl-thioacetate (SATA), and N-succinimidyl-3-(2-pyridyldithio) propionate (SPDP), 6-hydrazinonicotimide (HYNIC), $N_3S$ and $N_2S_2$ can be used in well-known procedures to synthesize biotin amide analogs or biotin compounds. For example, biotin can be conjugated via DTPA using the bicyclic anhydride method of Hnatowich et al. (Int. J. Appl. Radiat. Isotop. 33, 327 (1982). In addition, sulfosuccinimidyl 6-(biotinamido) hexanoate (NHS-LC-biotin (which can be purchased from Pierce)), "biocytin", a lysine conjugate of biotin, can be useful for making biotin compounds due to the availability of a primary amine. In addition, corresponding biotin acid chloride or acid precursors can be coupled with an amino derivative by known methods. Thus, preparation of a variety of moieties conjugated to a biotin compound is possible. Furthermore, a biotin compound can be conjugated to a solid support, if desired.

The term "conjugated," as used herein, means ionically or covalently linked or attached (e.g., by use of a derivatizing reagent).

The term "biotin-binding compound" refers to a compound which can tightly but non-covalently bond biotin compounds. Biotin-binding compounds include avidin and streptavidin, as well as derivatives and analogs thereof, including avidin or streptavidin conjugated to other moieties (such as other proteins). Preferred biotin-binding compounds include avidin, streptavidin, covalent adducts of avidin and streptavidin, and fusion proteins having a domain which has biotin-binding activity. In certain embodiments, anti-biotin antibodies can be used as the biotin-binding compound. The covalent linkage of biotin-binding compounds such as streptavidin is well known, and some streptavidin-conjugated solid supports are commercially available (e.g., Dynabeads magetic microbeads, Dynal, Hamburg, Germany). Thus, biotin-binding compounds linked to an insoluble support are usefull in the present invention.

A "solid support" refers to a support which is solid or can be separated from a reaction mixture by filtration, precipitation, magnetic separation, or the like. Exemplary solid supports include beads (such as Sepharose, Sephadex, polystyrene, polyacrylamide, cellulose, Teflon, glass, (including controlled pore glass), gold, or platinum); flat supports such as membranes (e.g., of cellulose, nitrocellulose, polystyrene, polyester, polycarbonate, polyamide, nylon, glass fiber, polydivinylidene difluoride, and Teflon); glass plates, metal plates (including gold, platinum, silver, copper, and stainless steel); silicon wafers, mictrotiter plates, and the like. Flat solid supports can be provided with pits, channels, filter bottoms, and the like, as is known in the art.

A "biotin compound:biotin-binding compound complex" refers to a noncovalent complex formed by the binding of a biotin compound to a biotin-binding compound.

The term "analyzing," as used herein, refers to detection of, or characterization of, a molecule or moiety. Thus, a molecule can be analyzed by a variety of known techniques, including spectrometric techniques such as UV/VIS, IR, or NMR spectroscopy, mass spectrometry, chromatography, electrophoresis, or other methods known in the art, or combinations thereof. "Analyzing" can also include methods such as sequencing of nucleic acids.

The term "ammonia", as used herein, refers to $NH_3$, or any salt thereof. Thus, depending upon the solvent used, and the pH of the solvent, ammonia may be present as $NH_3$, or may be in the form of an ammonium salt or compound. For example, ammonia in aqueous solution can exist largely as ammonium hydroxide (depending on the pH), but is generally referred to herein as "ammonia."

The term "amine", as used herein, refers to a compound having the structure $NR'_3$, or $N^+R'_4$ in which $R'$ is a hydrogen, alkyl (including cycloalkyl), alkenyl, alkynyl, or aryl group, and can be independently selected for each occurrence. Two or more $R'$ groups can be selected such that they form, together with the nitrogen atom to which they are attached, a cyclic amine (for example, pyrrolidine or piperidine). In certain embodiments, aromatic amines such as pyridine are contemplated for use in the subject methods. Where an $R'$ group is alkyl, the alkyl group can have from one to twelve carbon atoms in a straight or branched chain. Lower alkyls (having from one to six carbon atoms in a branched or straight chain) are preferred. A preferred aryl group is phenyl, which can be substituted or unsubstituted. Exemplary amines include ammonia, methylamine, diethylamine, aniline, and diisopropylethylamine. Further, quaternary amines, such as tetrabutyl ammonium (e.g., as tetrabutylammonium hydroxide), can be used in the methods of the invention. Other nitrogen-containing compounds, including hydrazine, and derivatives and analogs thereof, can also be used in the invention.

It is believed that small amines (i.e., those molecules with small steric bulk, e.g., where at least one $R'$ is hydrogen or a small alkyl group such as methyl) are more effective than larger amines at dissociating biotin compound: biotin-binding compound complexes. Thus, amines in which each $R'$ is sterically small (e.g., hydrogen or a small alkyl group such as methyl) are preferred. In particular, primary amines are more preferred than secondary amines, which are in turn more preferred than tertiary amines, which are in turn more preferred than quaternary amines. In general, an amine will be selected according to factors such as cost, efficacy, ease of handling, ease of purification of the desired products, and the like. Ammonia is a most preferred amine, at least in part because ammonia effectively cleaves biotin complexes and is inexpensive, readily handled as either the gas or ammonium hydroxide in solution, and easily removed when reaction is complete (e.g., by lyophilization). As described in more detail below, the use of ammonia as the cleaving reagent permits facile purification of biotin compounds by removal of excess ammonia under a vacuum. Thus, in certain embodiments, an amine that is sufficiently volatile to be removed by lyophilization is preferred. However, other methods of purifying a biotin compound or biotin-binding compound (or a mixture of both) can be employed, including, for example, dialysis, gel electrophoresis, capillary zone electrophoresis, affinity chromatography, crystallization, column chromatography (e.g., gel or ionic exchange chromatography), HPLC, and the like.

The methods of the invention are particularly useful in purification of biotinylated compounds. For example, a biotinylated compound can readily be separated from non-biotinylated compounds simply by contacting a reaction mixture with immobilized biotin-binding compound, e.g., covalently bound to a solid support, followed by separation and washing of the immobilized complex of the biotin compound with the biotin-binding compound. The biotinylated molecule can then be isolated by dissociation of the biotin: biotin-binding compound complex, followed by separation of the biotin compound from the solid support. The purified biotinylated compound can then be lyophilized, further purified by conventional techniques, or the like. The skilled artisan will appreciate that a biotin-binding compound can be purified by an analogous process, e.g., by contacting a reaction mixture containing a biotin-binding compound with an immobilized biotin compound to form a complex, followed by purification and subsequent dissociation of the complex.

In the case of biotinylated nucleic acids, the biotin-streptavidin system can be used for the isolation of either single- or double-stranded nucleic acids, e.g., DNA. A preferred application is the isolation of a double-stranded PCR product, the subsequent removal of the non-biotinylated strand and the downstream processing of the single strands (Mitchell, L. G., et al. (1994) "Advances in Biomagnetic Separation," Eaton publishing, Natick, Mass., USA, p. 31–48). Currently, denaturing of double-stranded products on streptavidin Dynabeads is preferably done using 0.1 M NaOH. Other pplications include the purification of PCR and LCR products as well as purification of DNA sequencing products (Jurinke, C., et al., (1996) *Anal. Biochemistry*, 237, 174–181).

The exact mode of action of ammonia and other amines on biotin decomplexation is not known. It is believed that the pH of the reaction system is important to effectively decomplex biotin and biotin-binding compounds within a reasonable time. However, it is known that biotin complexes are stable up to relatively high pH in the absence of ammonia. In particular, 0.1N sodium hydroxide solution (at a pH of about 13) is less effective at cleaving biotin compound:biotin-binding-compound complexes than is 25% ammonium hydroxide solution. Ammonia is known to be a strong hydrogen bond donor-acceptor. Without wishing to be bound by any theory, it is believed that the ammonia molecules are small enough to diffuse into the biotin complex and disrupt the bonding (e.g., hydrogen bonding) of the biotin moiety with a biotin-binding compound. The biotin compound retains the ability to bind to a biotin-binding compound after treatment with ammonia, and the biotin moiety can remain substantially intact.

Thus, the pH of the reaction mixture can affect the rate of complex dissociation. In preferred embodiments, the pH of the reaction mixture is in the range from about 7.0 to about 14.0, more preferably from about 8.0 to about 13.0.

The concentration of the ammonia or other amine is also important. A preferred concentration is at least about 5% ammonia or amine, more preferably about 10%, and still more preferably at least about 15% (w/v). Higher concentrations will generally result in more rapid complex dissociation. Accordingly, a concentration of about 25–28% is preferred. An ammonia concentration of 25–28% can be readily achieved with commercially available ammonium hydroxide solutions.

The temperature at which the cleavage reaction is performed also affects the rate of complex dissociation. The temperature will be chosen according to considerations such as the rate of reaction (which will be faster at higher temperatures) and the stability of the components (e.g., the biotin compound and biotin-binding compound), which will generally be less stable at higher temperatures. In preferred embodiments, the temperature is in the range from about 25° C. to about 100° C., more preferably from about 40° C. to about 80° C. A preferred temperature is about 60° C. In certain embodiments, it may be preferred to perform the cleavage reaction under pressure (e.g., in the range of 1–200 atm), or in a sealed reaction vessel (such as a sealed tube or bomb).

The reaction mixture can be an aqueous mixture such as a solution or suspension, or a non-aqueous solvent can be employed, including, e.g., methanol, ethanol, acetonitrile, dimethylformamide, and the like. Mixtures of solvents can also be employed (e.g., water/methanol or water/acetonitrile). The solvent will in general be selected to be compatible with at least one of the biotin compound, the biotin-binding compound, or the amine. The choice of an appropriate solvent will be routine to the skilled artisan. Aqueous solvents are generally preferred.

Of course, the skilled artisan will appreciate that not all biotin compounds (or biotin-binding compounds) will be stable to all reaction conditions. For example, where a biotin compound is a biotinylated protein (e.g., a biotinylated antibody), vigorous conditions such as high pH and high temperature can denature the protein moiety. Thus, conditions will in general be selected to avoid undesired denaturation or destruction of at least one of the biotin compound or biotin-binding compound.

The method of the invention can be used to purify a biotin compound. For example, in a preferred embodiment, the method comprises the steps of contacting a biotin compound:biotin-binding compound complex with an effective amount of ammonia, under conditions such that the complex is dissociated, thereby forming a biotin compound and a biotin-binding compound. In certain preferred embodiments, the method includes, prior to the dissociating step, the step of purifying the biotin compound:biotin-binding compound complex by separating the complex from at least one impurity. Thus, by contacting a reaction mixture comprising a biotin compound with a solid support comprising an immobilized biotin-binding compound, followed by purification of the complex and subsequent release of the biotin compound from the complex by treatment with an amine, the biotin compound can be purified from a complex reaction mixture. Examples of the purification of, e.g., nucleic acids, by the methods of the invention are provided below. It has been found that the inventive methods are particularly useful where a biotin compound is to be analyzed by mass spectrometry subsequent to complex dissociation. In this embodiment, use of ammonia as the amine is preferred.

Thus, in a preferred embodiment, the invention provides a simple method for isolating biotin-conjugated molecules from biotin-streptavidin complexes. The method is compatible with subsequent mass spectrometric analysis of the isolated biotin-conjugated molecules.

The subject method provides a mass spectrometric-compatible process for releasing intact and non-modified biotinylated molecules from biotin-streptavidin complexes by a brief treatment of a complex with an amine (e.g., ammonia, which can be supplied as ammonium hydroxide), preferably at slightly elevated temperatures. Several mass spectrometer formats can be used for detection of the recovered products, including ionization by matrix-assisted laser desorption/ionization (MALDI), continuous or pulsed electrospray (ES), or massive cluster impact (MCI); and detection formats including linear or reflectron time-of-flight (TOF), single or multiple quadrupole, single or multiple magnetic sector, Fourier Transform ion cyclotron resonance (ICR), ion trap, and combinations thereof. For ionization, numerous matrix/wavelength combinations (MALDI) or solvent combiantions (ESI) can be employed.

This new method is of outstanding importance for all processes which are based on a fast and quantitative recovery of biotin-conjugated materials from biotin-streptavidin complexes and subsequent enzymatic reactions and analysis via techniques negatively influenced by organic impurities such as formamide. These include, for example, analysis of PCR or DNA sequencing products with mass spectrometry for diagnostic purposes.

FIG. 1 illustrates one embodiment of the invention. FIG. 1 is a schematic drawing of the purification of biotinylated PCR products where the reaction was carried out in solution. In this scheme, A represents the biotinylated PCR product, R represents reaction components and impurities and H represents the streptavidin coated solid support (e.g. streptavidin Dynabeads or multititer plates).

In step 1 of this embodiment, a PCR reaction is carried out with at least one biotinylated primer. The biotin group can be attached either on the 5'-hydroxyl group of the primer or at an internal base. By choosing appropriate conditions, as are known in the art, in the presence of buffer, template, deoxynucleotides and a thermostable DNA polymerase (collectively depicted as R) a biotinylated PCR product (A) will be generated.

Since short primers will immobilize more efficiently than longer PCR products, in step 2 of FIG. 1, the non-extended primer is removed by ultrafiltration through size-exclusion membranes, according to procedures described in the art. After ultrafiltration, the PCR product will sometimes be accompanied by enzyme and/or some buffer components (R). For further purification, the PCR product can be complexed to a solid support (H) having a biotin-binding compound immobilized thereon (e.g., streptavidin or avidin). The complexation conditions may vary; suitable conditions include incubation at ambient temperature in the presence of 2M sodium chloride or ammonium chloride, and a pH of around 7.5. The nature of the solid support may vary, and include, e.g., magnetic particles (e.g., beads), multititer plates with or without filter plates, glass, silicon wafers with or without pits, plastic, paper, flat arrays, capillaries, agarose or sepharose. Streptavidin-coated magnetic beads (Dynabeads, Dynal, Inc) are preferred.

In step 3 of FIG. 1, due to the stability of the biotin-streptavidin complex, intensive washing can be performed to remove all excessive reaction components prior to the recovery of the PCR product. The complexed and purified PCR product is then treated with a small volume of 25% ammonium hydroxide, preferably at about 50–60° C., to overcome the biotin-streptavidin interaction.

In step 4 of FIG. 1, the pure PCR product is accompanied only by ammonium hydroxide. The ammonium hydroxide can easily be removed by lyophilization or ethanol precipitation, both methods well known in the art. The pure PCR product is redissolved, most preferably in ultrapure water. Other conditions can be chosen, for example varying buffers as a solvent. The PCR product now can be employed in downstream applications, e.g., enzymatic reactions or detection, for example, via mass spectrometry or gel electrophoresis in slab gels or capillaries, as described in the art.

Using ammonia for the dissociation of the biotin-streptavidin complex is of special interest for detection of DNA using mass spectrometry. It is known that heterogenity of cations leads to a broadening of mass signal and interferes with the detection process. Thus, mass spectrometric detection would benefit if cation homogeneity could be achieved. The methods of the invention provide DNA with a homogeneous cation distribution, because after treatment with ammonia, most of the phosphate groups will carry an ammonium counterion. Another advantage is that DNA with ammonium counterions is known to have preferred properties for mass spectrometric (e.g. MALDI-TOF) MS analysis.

Figure 2:
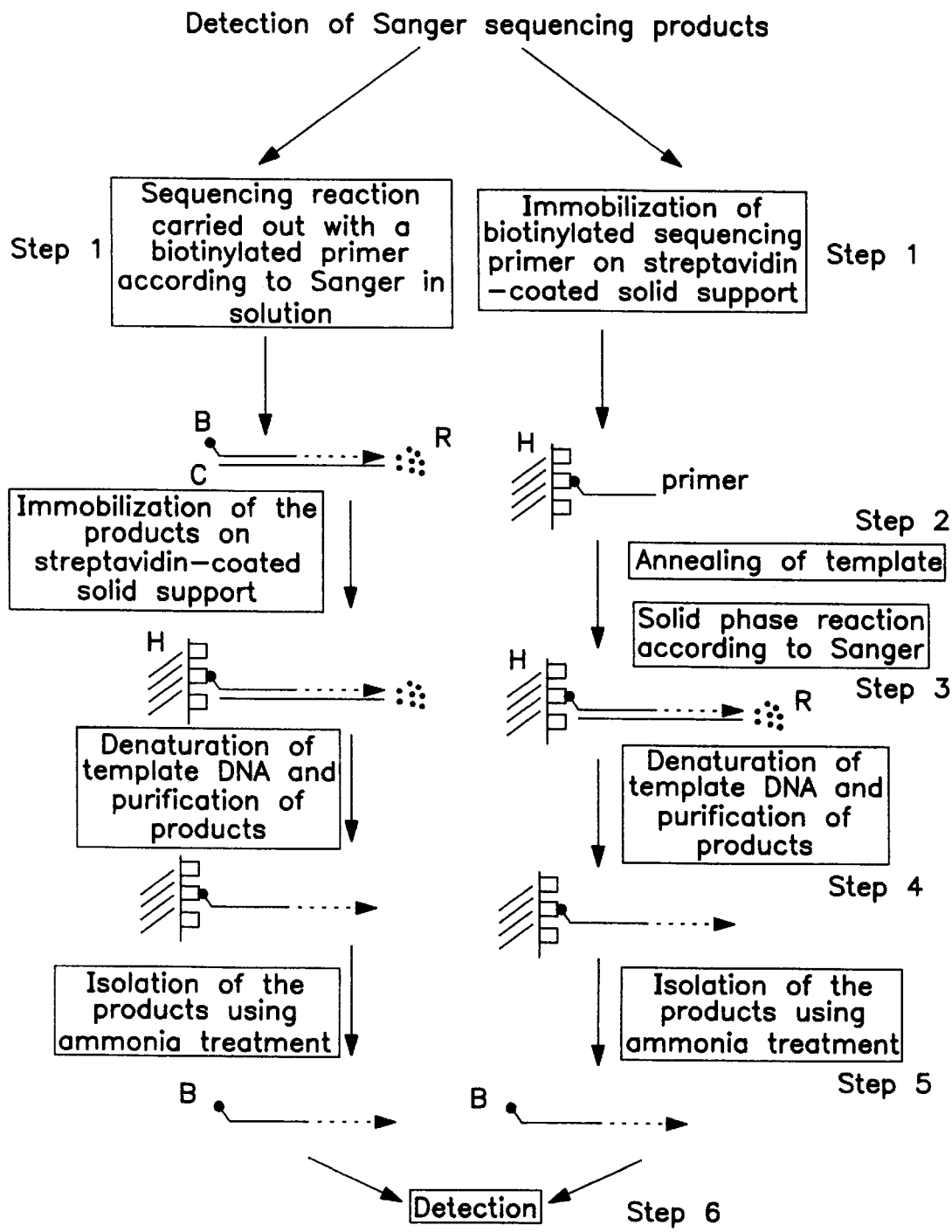
FIG. 2 is a schematic drawing of two different means for detecting Sanger sequencing products.

A second embodiment of the subject method is illustrated in FIG. 2. It features the detection of Sanger sequencing products and the use of a biotin-streptavidin complex in the process. FIG. 2 is a schematic drawing of two different means for detecting Sanger sequencing products. On the left side of this scheme, a biotinylated primer is used and the reaction is carried out in solution with subsequent immobilization, purification, ammonium hydroxide treatment and detection. On the right side, the reaction is performed as a solid phase reaction. In this scheme B represents biotinylated primer extension products, R represents reaction components and impurities, C represents template DNA, and H represents the streptavidin-coated solid support.

As shown in FIG. 2, left column, in the first step, a Sanger sequencing reaction is carried out in solution with a biotinylated primer. The products arising from this primer extension reaction are double-stranded nucleic acids consisting of the extended biotinylated primer (B) and the template strand (C). In the second step, as show in FIG. 2, the biotinylated complex is immobilized on a streptavidin-coated solid support (H) (as described above). Due to the stability of the biotin-streptavidin complex, the immobilized complex can be separated from excess reaction components, by-products and impurities (R) as previously described. In the third step the template DNA is denatured from the biotinylated primer extension products (B) by methods well known in the art. A solution of 8 M urea was used for the purpose of denaturation. Further washing steps, preferably with ultrapure water, were employed to remove the urea and the template strand. In the fourth step the purified biotinylated sequencing product (B) was recovered through treatment with 25% ammonium hydroxide. Removal of ammonium hydroxide can be performed using ethanol precipitation or lyophilization, as described above. The biotinylated products can be resuspended in ultrapure water and analyzed by mass spectrometry or gel electrophoresis or subjected to further enzymatic reactions.

In a variation of this second embodiment, the sequencing reaction is carried out on a solid support. FIG. 2, right column, illustrates this variation. In the first step, the biotinylated primer is immobilized on a streptavidin-coated solid support (H). In the second step, a template strand is annealed to the immobilized biotinylated primer. In the third step a sequencing reaction, such as Sanger sequencing, is carried out. In the fourth step, reaction components and impurities (R) are removed through washing. The template is denatured from the biotinylated extended primer using urea as described above, and further washing steps are carried out. In step 5 the purified biotinylated extension products (B) are recovered through treatment with ammonium hydroxide as decribed above, and subjected to analysis, for example, via mass spectrometry, electrophoresis or futher enzymatic reactions.

Figure 3:
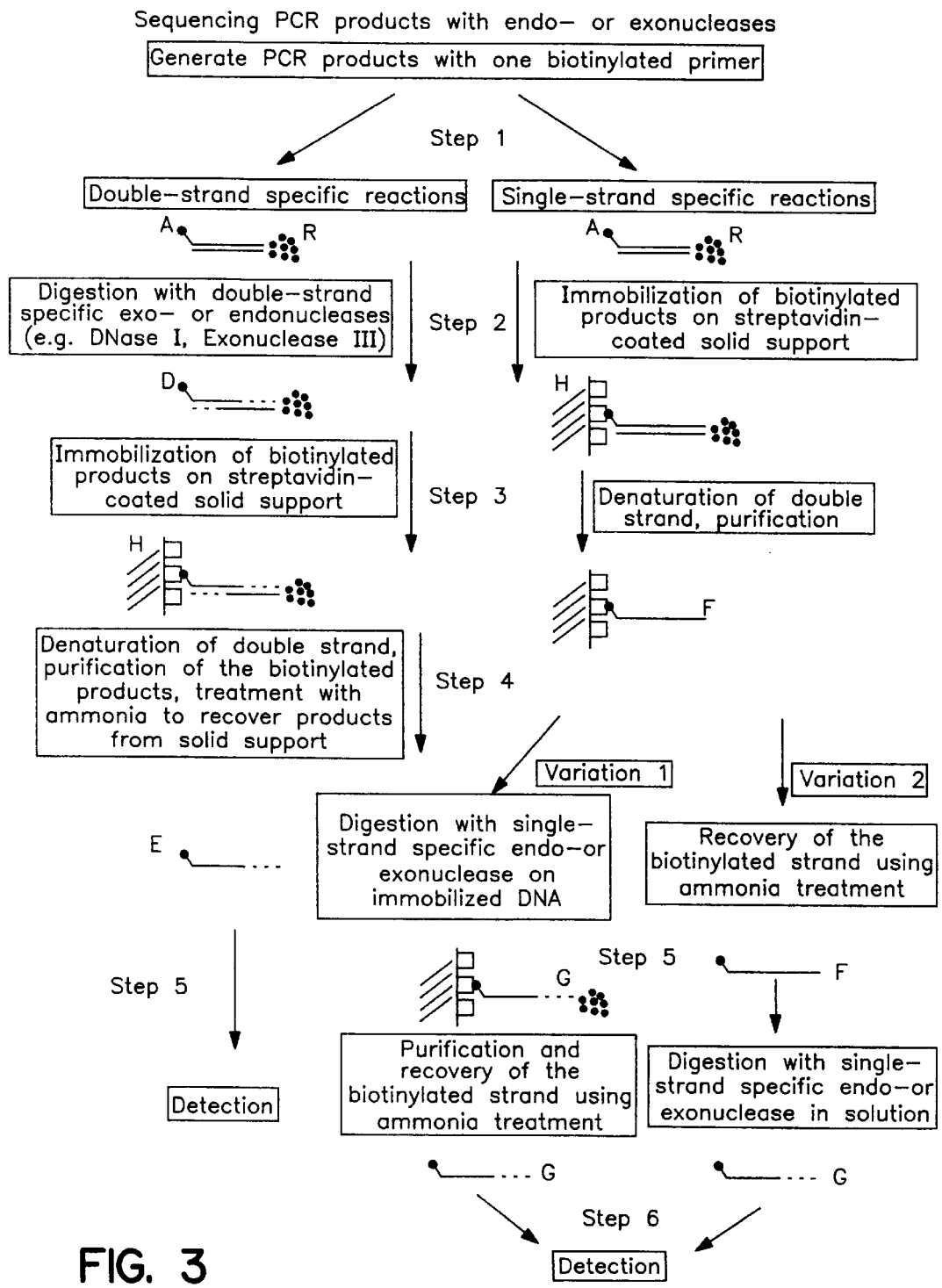
FIG. 3 is a schematic drawing of different means for detecting PCR digest products with single- or double-stranded specific endo- or exonucleases to generate DNA sequence information.

A third embodiment of the instant invention is illustrated in FIG. 3. FIG. 3 is a schematic drawing of different means for detecting PCR digest products with single- or double-stranded specific endo- or exonucleases to generate DNA sequence information. In this scheme, A represents biotinylated PCR product; D represents digested biotinylated PCR product; E represents biotinylated single-stranded PCR digest product; F represents undigested biotinylated single-stranded PCR digest product; G represents digested biotinylated single-stranded PCR digest product; H represents a streptavidin coated solid support; and R represents reaction components and impurities.

This embodiment features the sequencing of PCR products with endo- or exonucleases and the use of the biotin-streptavidin complex in this process. In the first step, as shown in FIG. 3, left column, a PCR reaction is carried out with one biotinylated primer. Prior to further reactions, unincorporated primers are removed using ultrafiltration through a molecular weight cutoff membrane (as decribed above). In the second step, the biotinylated PCR product (A) is subjected to digestion with double-strand specific enzymes. This can be carried out using, for example, DNaseI, which nicks the double strand DNA statistically at each phosphodiester bond. The reaction can be carried out in a way such that each double strand arising from the PCR reaction is nicked once statistically (Low, C. M. L. et al. (1984) *Nucleic Acids Res.* 12 4865–4879). A second approach is the use of exonuclease III, which digests double-strand DNA from the 3' end of the molecule. A third approach uses type II restriction-endonucleases to carry out RFLPs in combination with subsequent analysis, for example, via mass spectrometry or electrophoresis. In the third step, the biotinylated digestion products (D) of step 2 are immobilized on a streptavidin-coated solid support (H) (as described above). In step 4, the immobilized biotinylated products are separated from reaction components and impurities (R) (as described above) and the hybridized non-biotinylated products are removed using a denaturing agent like urea (as described above for the second embodiment). The biotinylated products (E) are released from the solid support by treatment with ammonium hydroxide. After removal of the ammonium hydroxide using ethanol precipitation or lyophilization, the biotinylated products (E) can be resuspended in, for example, ultrapure water and analyzed, for example, via mass spectrometry or electrophoresis.

A variation of this embodiment features the sequencing of PCR products with single-strand-specific endo- or exonucleases and the use of a biotin-streptavidin complex in the process. It is illustrated in FIG. 3 ("Variation 1"). The biotinylated PCR product (A) is immobilized on a streptavidin-coated solid support (H) after ultrafiltration (step 2). In step 3 the non-biotinylated strand is denatured using urea, and further washing steps are carried out In step 4 the immobilized biotinylated single-stranded PCR product (F) can be digested with a single-strand specific endo- or exonuclease. For endonuclease digestion, mung bean nuclease or SI nuclease is preferred, while for exonuclease digestion, calf spleen or snake venom phosphodiesterase is used. The latter is preferred. The immobilized digestion products (G) are purified with further washing in step 5, and are recovered from the solid support using treatment with ammonium hydroxide. As described previously, the recovered biotinylated products (G) can be analyzed after ethanol precipitation or lyophilization.

In another variation of this embodiment (shown in FIG. 3 as "Variation 2"), in step 5 an immobilized single-strand PCR product (F) (as described above in step 3) is treated with ammonium hydroxide to recover the biotinylated single-strand PCR product (F). The ammonium hydroxide is removed using, e.g., ethanol precipitation or lyophilization and the DNA is resuspended in ultrapure water. In step 5, the isolated single stranded PCR product (F) is digested with a single-strand specific endo- or exonuclease, preferably mung bean nuclease, S1 nuclease or snake venom phosphodiesterase, respectively.

In step 6 the digestion products (G) are then analyzed, for example, via mass spectrometry or electrophoresis.

Among the advantages of the methods of the invention are: i) there is no need to use harsh, denaturing or toxic organic compounds such as phenol or formamide, ii) biotin-streptavidin complexes can be cleaved under mild conditions, iii) volatile amines, such as ammonia, can be easily and rapidly removed (for example by lyophilization), iv) the recovered material can be subjected to enzymatic reactions or, e.g., mass spectrometric analysis, without further purification, v) a simultaneous biotin-streptavidin complex cleavage and cation exchange. Accordingly, the process of the invention will considerably extend the applicability of the biotin-streptavidin system by providing a mild and selective procedure to recover the biomolecules after immobilization for further enzymatic reactions or analysis.

EXEMPLIFICATION

The following examples illustrate, but do not limit, the process of the present invention.

Examples 1–5 illustrate the utility of the subject methods in various applications in diagnostics and DNA sequencing. In general, the illustrated examples involve at least some of the following steps:
1. Performing (a) an enzymatic reaction employing biotinylated DNA in solution or (b) DNA immobilized on a solid support via a biotin-streptavidin complex, respectively.
2. Separation of excess biotinylated primer, if necessary, using size exclusion ultrafiltration membranes.
3. Immobilization of the products of step 1a by complexing the biotinylated DNA to a biotin-binding protein supported on a solid phase.
4. Separating the complex of step 3 or step 1b from the liquid phase. Further options include washing to remove reaction contents and impurities, conditioning of immobilized nucleic acids, enzymatic reactions and isolation of the non-biotinylated strand of a DNA duplex for downstream applications.
5. Treating the separated and manipulated complex of step 4 with ammonium hydroxide for isolation of biotinylated molecules.
6. Complete removal of ammonium hydroxide by lyophilization or precipitation with ethanol.
7. Downstream processing of isolated material, e.g. analysis of products by MALDI-TOF MS or further enzymatic reactions.

As described above, the effect of ammonium hydroxide on the immobilized nucleic acids is a function of temperature and time of incubation. If the immobilized material is incubated for short times at ambient temperature, the main process is the denaturation of the immobilized double-stranded molecules. However, incubation of immobilized DNA with ammonium hydroxide at elevated temperatures (preferably 37–80° C.) leads to the dissociation of the biotin-streptavidin complex.

Example 1

MALDI-TOF MS Spectrum of a Biotinylated Oligodeoxynucleotide Cleaved from Streptavidin Dynabeads Using Ammonium Hydroxide For this example, 100 pmol biotinylated oligodeoxynucleotide (20 mer), 5'd(bio-AGCTCTATATCGGGAAGCCT)3' (SEQ ID NO:1), were immobilized on 50 $\mu$l streptavidin Dynabeads M-280. The beads were prepared according to the instructions of the manufacturer. The beads were finally resuspended in 50 $\mu$l of B/W-buffer (10 mM Tris-HCl, pH 7.5, 1 mM EDTA, 2 M NaCl). The oligodeoxynucleotide was added in a volume of 1 $\mu$l and the reaction mixture was incubated for 30 minutes at ambient temperature. After immobilization, the beads were washed twice with 100 $\mu$l of ammonium citrate buffer (0.07 M). The beads were washed once with ultrapure water, 25 $\mu$l of a 25% solution of ammonium hydroxide were added, and the beads were carefully resuspended. The suspension was incubated at 60° C. for 10 minutes, and the beads were separated from the solution using a magnetic particle collector (Dynal, Hamburg, Germany). The supernatant was saved and the procedure was repeated once. Both supernatants were collected in a single tube. The solution was lyophilized for 30 minutes, and redissolved in 4 ||l of ultrapure water. From this solution 0.5 $\mu$l were analyzed with MALDI-TOF mass spectrometry (FIG. 4) as described in example 2, step 4.

Figure 4:
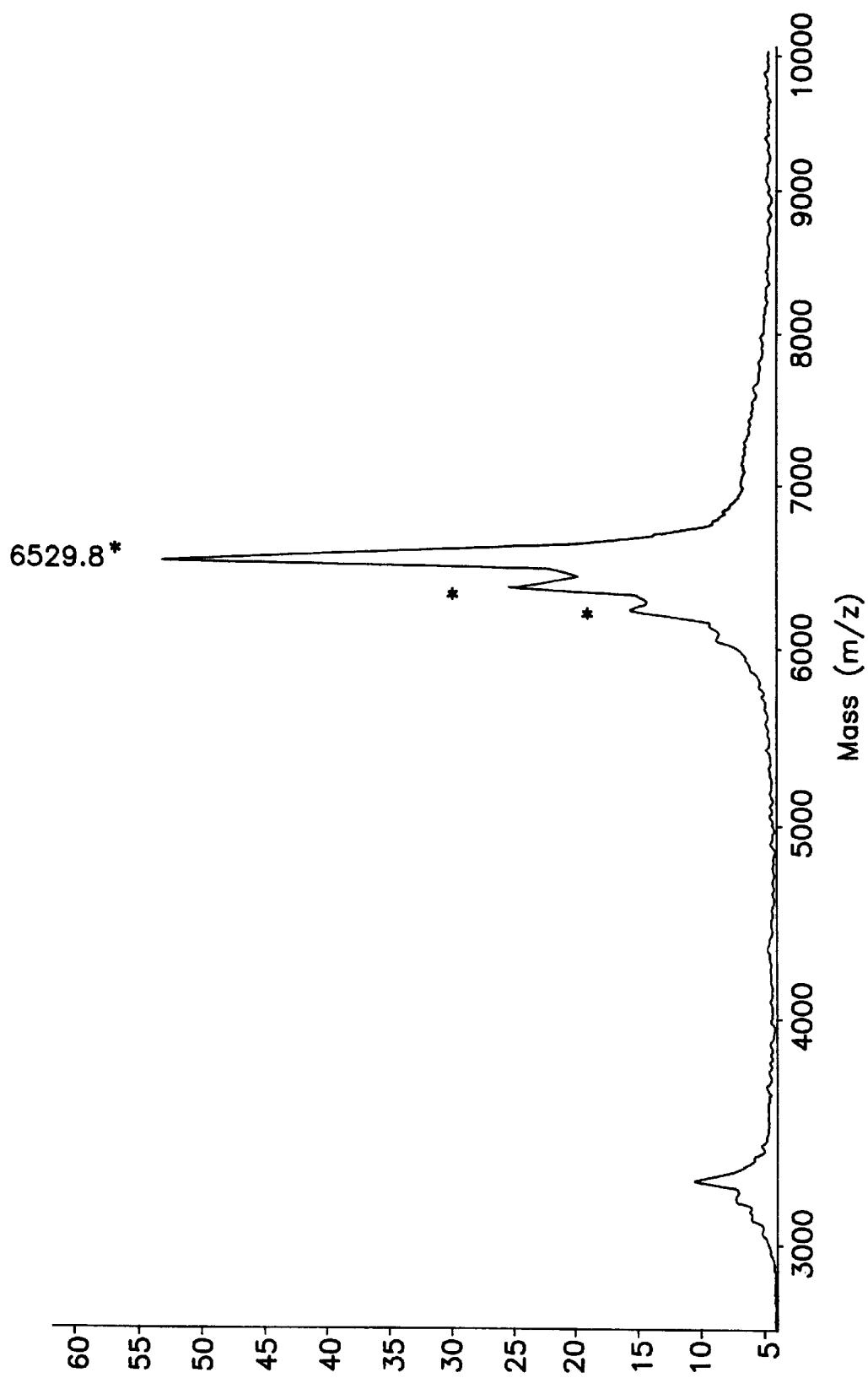
FIG. 4 shows a MALDI-TOF MS spectrum of a biotinylated 20 mer oligodeoxynucleotide (SEQ ID NO:1) immobilized on streptavidin Dynabeads and recovered using the method as described in Example 1.

FIG. 4 shows a MALDI-TOF MS (15 shots, laser power 44) spectrum of a biotinylated 20 mer oligodeoxynucleotide (SEQ ID NO:1) immobilized on streptavidin Dynabeads and recovered using the method described above. The theoretical mass value of the biotinylated oligodeoxynucleotide is 6522 Da. The mass value obtained is 6529.8 Da, in agreement with the predicted mass. The spectrum demonstrates that a biotinylated oligodeoxynucleotide is removed from the beads. Signals marked with an asterisk are due to depurination which occurs in the process of ionization and desorption also if ammonium hydroxide is not applied.

This Example demonstrates that biotinylated DNA can be recovered from a biotin-streptavidin complex using ammonium hydroxide at elevated temperatures. The oligodeoxynucleotide and the attached biotin group remain intact and unmodified during this process. This can be concluded because no change of molecular weight of the original molecule was observed by MALDI-TOF mass spectrometric analysis after subjecting an oligodeoxynucleotide to the described procedure. Further experiments demonstrated that the recovered biotinylated molecule can be complexed again to streptavidin, also suggesting an intact biotin group.

Example 2

MALDI-TOF MS Analysis of PCR Products Purified Via Streptavidin Dynabeads and Subsequent Removal from the Beads Using Ammonium Hydroxide Step 1

PCR was performed with 1 $\mu$l of a first set of PCR primers directed against the gene for the core protein of hepatitis B virus. The nested amplification product has a length of 67 bp. 100 pmol of each primer, 2.5 u Pfu(exo-) DNA polymerase (Stratagene, Heidelberg, Germany), a final concentration of 200 µM of each dNTP and 5 µl 10×Pfu buffer (200 mM Tris-HCl, pH 8.75, 100 mM KCl, 100 mM $(NH_4)_2SO_4$, 20 mM $MgSO_4$, 1% Triton X-100, 1 mg/ml BSA, Stratagene, Heidelberg, Germany) were used in a final volume of 50 µl. The reactions were performed in a thermocycler (OmniGene, MWG-Biotech, Ebersberg, Germany) using the following temperature program: 94° C. for 1 minute, 60° C. for 1 minute and 72° C. for 1 minute with 20 cycles. Sequence of oligodeoxynucleotide primers (purchased HPLC-purified from MWG-Biotech, Ebersberg, Germany):

HBV 13: 5'-d(TTGCCTGAGTGCAGTATGGT-)3' (SEQ ID NO:2)

HBV 15bio: 5'd(bio-AGCTCTATATCGGGAAGCCT)3' (SEQ ID NO:3)

Step 2

Purification of the PCR products obtained in step 1, above, was done according to the following procedure: Ultrafiltration was performed using Ultrafree-MC filtration units (Millipore, Eschbom, Germany) according to the protocol of the manufacturer, with centrifugation at 8000 rpm for 20 minutes. 25 µl (10 µg/µl) streptavidin Dynabeads M280 (Dynal, Hamburg, Germany) were prepared according to the instructions of the manufacturer and resuspended in 25 µl of B/W buffer (10 mM Tris-HCl, pH 7.5, 1 mM EDTA, 2 M NaCl). This suspension was added to the PCR samples (still in the filtration unit) and the mixture was incubated with gentle shaking for 15 minutes at ambient temperature. The suspension was transferred to a 1.5 ml Eppendorf tube and the supernatant was separated with the aid of a magnetic particle collector, MPC, (Dynal, Hamburg, Germany). The beads were washed twice with 50 µl of 0.07 M ammonium citrate solution, pH 8.0 (the supernatant was removed each time using the MPC).

Step 3

To remove the PCR product (a double strand of 67 base pairs), the beads were resuspended in 25 µl of 25% $NH_4OH$ Suprapur (Merck, Darmstadt, Germany) and incubated at 60° C. for ten minutes. The supernatant was removed and saved, and the $NH_4OH$ treatment was repeated once. Both supernatants were dried in a speedvac and resuspended in 4 µl of ultrapure water (MilliQ UF plus, Millipore, Eschborn, Germany). For MALDI-TOF MS analysis, 0.5 µl of this preparation was used.

Step 4

Figure 5:
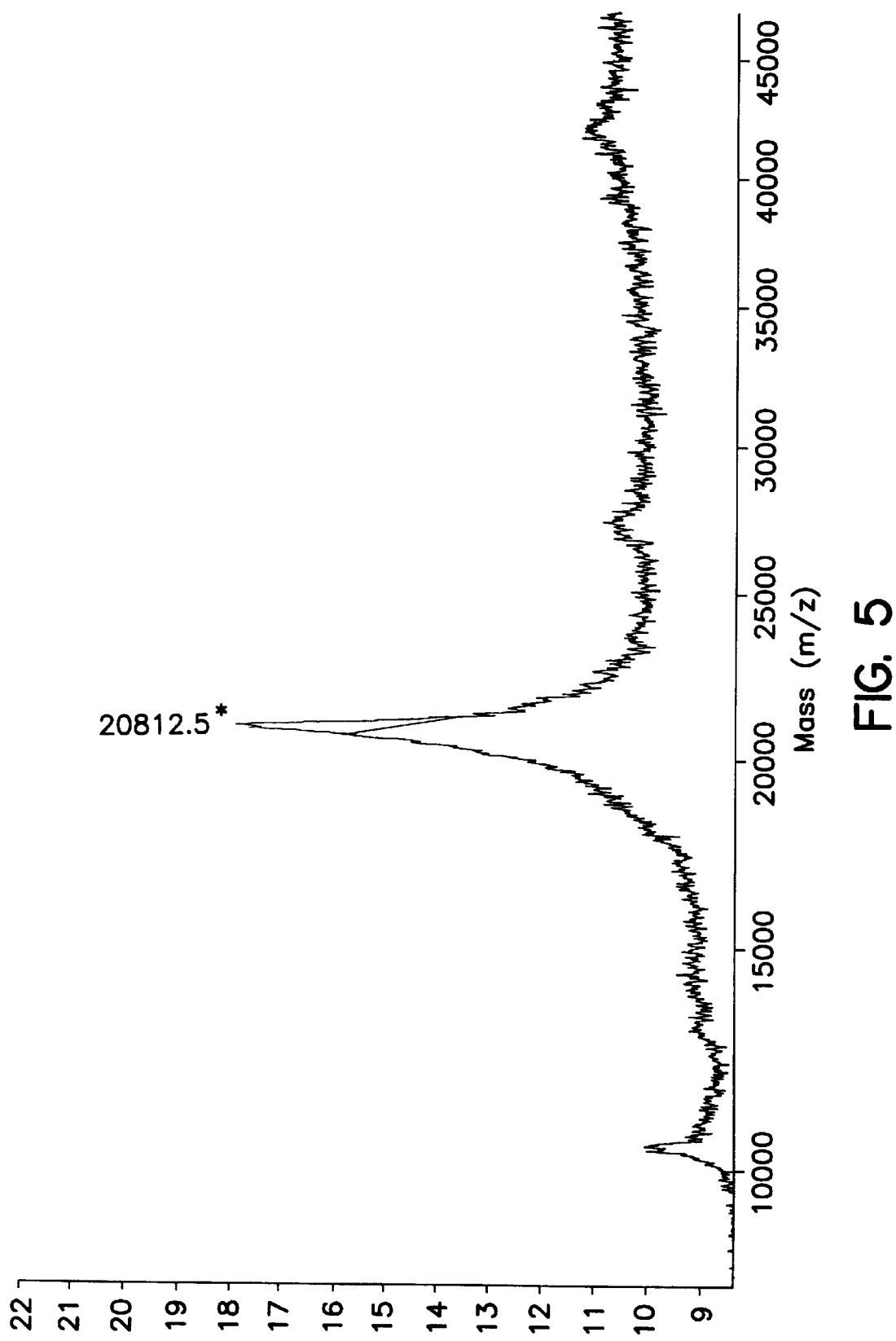
FIG. 5 shows a MALDI-TOF MS spectrum of a PCR product from the hepatitis B core antigen coding DNA region, purified with streptavidin Dynabeads and recovered from the beads using ammonium hydroxide, as described in Example 2.

Half a microliter (0.5 µl) of the sample was pipetted onto the sample holder, then immediately mixed with 0.5 µl of matrix solution (0.7 M 3-hydroxypicolinic acid in 50% acetonitrile, 70 mM ammonium citrate). This mixture was dried at ambient temperature and introduced into the mass spectrometer (FIG. 5). All spectra were taken in positive ion mode using a Finnigan MAT Vision 2000 (Finnigan MAT, Bremen, Germany), equipped with a reflectron (5 keV ion source, 20 keV postacceleration) and a 337 nm nitrogen laser. Calibration was done with a mixture of a nucleic acid 40 mer and 100 mer. Each sample was measured with various laser energies. In the negative (control) samples, the PCR product was not detected at low or high laser energies. In the positive samples, the PCR product was detected at different places of the sample spot and also with varying laser energies.

FIG. 5 shows a MALDI-TOF MS (15 shots, laser power 48) spectrum of a PCR product from the hepatitis B core antigen-coding DNA region, purified with streptavidin Dynabeads and recovered from the beads using ammonium hydroxide, as described above.

The theoretical mass value of the non-biotinylated strand is 20792.4 Da. The theoretical mass value of the biotinylated strand is 20886.9 Da. The average mass of both strands is 20839.7 Da. The mass value of the signal obtained is 20812.5 Da. Since double-stranded DNA molecules are denatured during the process of ionization and desorption, the PCR products are detected as single-stranded molecules and the mass value obtained represents the average mass of both single strands.

This Example demonstrates that MALDI-TOF MS analysis of PCR products is compatible with the method described herein. Compared to the purification procedures currently used, the introduced combination of a streptavidin-coated solid support, a biotinylated analyte molecule and the recovery of the PCR product, using ammonium hydroxide, led to improved sample processing and analysis.

Example 3

MALDI-TOF MS Analysis of Sanger Sequencing Products Purified Using Streptavidin Dynabeads and Subsequent Treatment with Ammonium Hydroxide For the streptavidin-biotin purification, a biotinylated USP (universal sequencing primer), which was supplied HPLC-purified from Pharmacia Biotech (Freiburg, Germany), was used. The primer sequence was designed so that 10 bases downstream from the primer binding site would be sequenced. The reaction was carried out using the reagents from the sequencing kit for Sequenase Version 2.0 (Amersham, Arlington Heights, Ill., USA)

Step 1

For annealing primer and template, 40 pmol bioUSP (1 µl) and 40 pmol of template (1 µl) were incubated with 4 µl of Sequenase-Buffer (5×), heated to 65° C. for 2 min. and then slowly cooled down to ambient temperature. To the annealing mixture, 1 µl Mn-buffer (supplied in the kit by the manufacturer), 1 µl dithiothreitol (DTT), 2 µl ultrapure Water (MilliQ, Millipore, Eschborn, Germany) and 2 µl diluted Sequenase 2.0 (6 U, diluted with pyrophosphatase) were added.

After the addition of the Sequenase, 3 µl of the reaction mix were pipetted into each of the four termination mixes (A, C, G and T, each 4 µl). The mixtures were incubated at 34° C. for 20 minutes. Each reaction was stopped with 1.5 µl 500 mM EDTA.

Step 2

After stopping the termination reaction with EDTA, the sequencing products were immobilized on streptavidin beads prepared according to the protocol of the manufacturer. To each reaction, 20 µl of prewashed beads were added and incubated at ambient temperature for 15 minutes under gentle shaking. After immobilization, the beads were washed twice with B/W-buffer (see above) and once with ultrapure water. The template was then denatured from the immobilized strand with ultrapure water at 95° C. for 2 minutes. After denaturation the beads were washed twice with 0.07 M ammonium citrate and once with ultrapure water.

Step 3

The immobilized sequencing products were cleaved from the beads with 20 µl of 25% ammonia at 60° C. for 10 minutes; the cleavage reaction was performed twice and the supernatants combined. The samples were then lyophilized, resuspended in 4 µl ultrapure water and directly used for MALDI-TOF-MS.

Step 4

The reaction products were analyzed using MALDI-TOF MS (56 shots, laser power 51) (FIG. 6) according to the procedure described in example 2, step 4.

Primer 17 mer (molecular weight 5744.4 Da):

5'd(bioGTAAAACGACGGCCAGT)3' (SEQ ID NO:4),
Template 50 mer (molecular weight 15338 Da):
5'd(TTGCGTACACACTGGCCGTCTTTTACAAC GTCGTGACTGGGAAAACCT C)3' (SEQ ID NO:5)

Both primer and template were synthesized (about 0.2 $\mu$mol) on a Milligen 7500 using $\beta$-cyanoethylphosphoamidite chemistry (Sinha, N. D., et al. (1984) *Nucleic Acids Res.* 12, 4539–4577), and purified via RP-HPLC.

Figure 6:
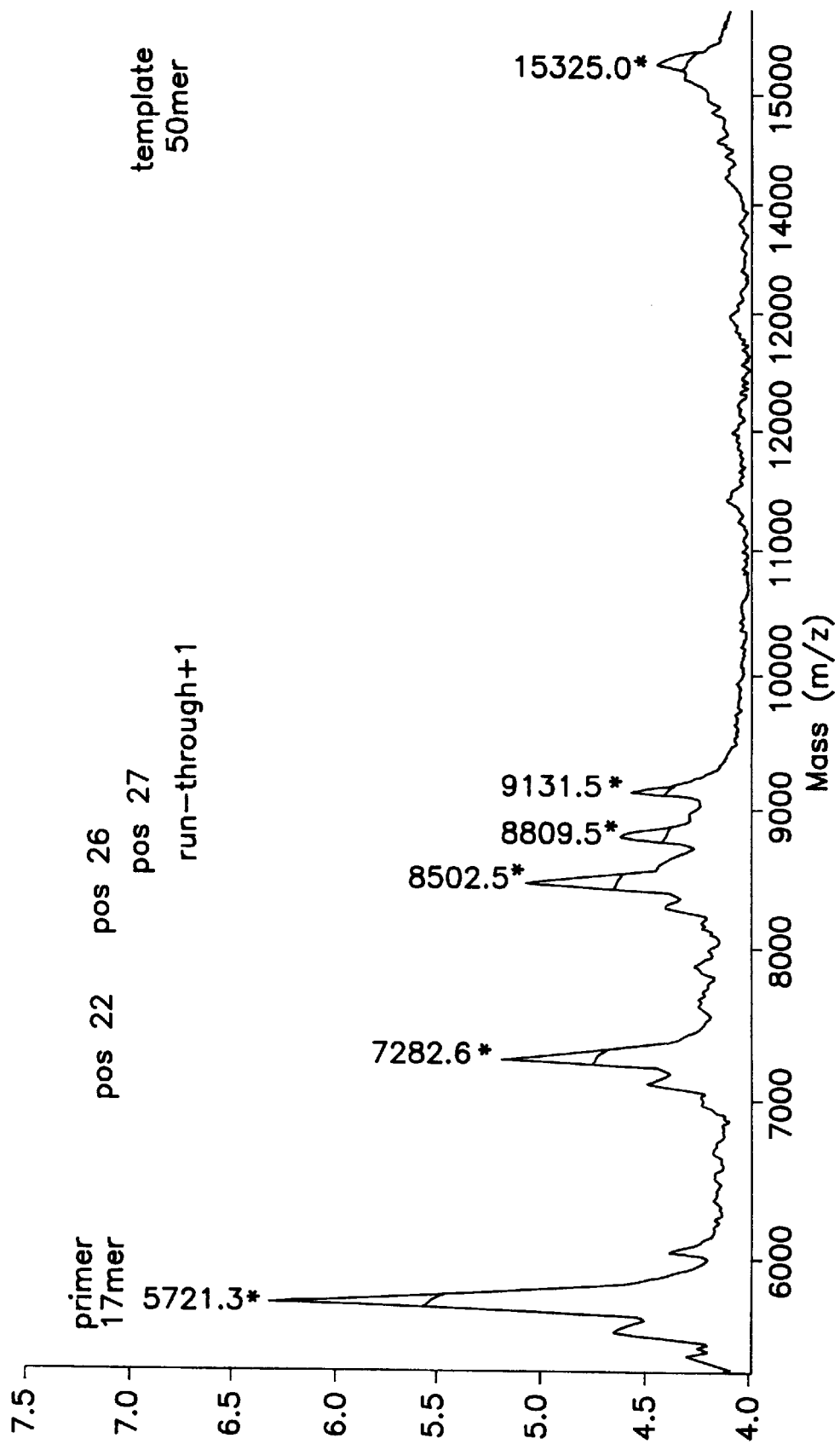
FIG. 6 shows the A-reaction of the Sanger sequencing reaction purified with M-280 streptavidin Dynabeads.

FIG. 6 shows the reaction of the Sanger sequencing reaction purified with M-280 streptavidin Dynabeads. The sequencing reaction was carried out in solution and the sequencing products were captured with Dynabeads. The reaction contents, such as salts, enzymes, dNTPs and dideoxynucleotide triphosphates (ddNTPs), were removed by washing, and the sequencing products were recovered for MALDI-TOF-MS analysis using ammonium hydroxide, as described above.

Three termination products were expected in the A-reaction with a length of 22-, 26- and 27 bases, respectively. These products are represented by the signals at 7282.6 Da, 8502.5 Da and 8809.5 Da, respectively. The signals at 5721.3 Da and 15325 Da represent primer and template, respectively. The signal at 9131.5 Da is due to a single-nucleotide extension of the run-through product.

This Example, and Example 4 and 5, infra, demonstrate the utility of the subject methods in DNA sequencing. This Example shows that the method is compatible with the analysis of conventional Sanger sequencing.

Example 4

MALDI-TOF-MS Analysis of Exonucleolytic Digestions of PCR Products

Step 1

The reaction mix contained 200 $\mu$M dCTP, dTTP and 200 $\mu$M $C^7$-deaza DATP and $C^7$-deaza dGTP, 100 pmol of forward and reverse primer, 100 ng M13mp18 RF, and 2.5 U of Pfu (exo-) DNA polymerase (Stratagene, Heidelberg, Germany) in a buffered solution (20 mM Tris-HCl, pH 8.75, 10 mM KCl, 10 mM $(NH_4)_2SO_4$, 2 mM $MgSO_4$, 0.1% Triton X-100, 0.1 mg/ml BSA, Stratagene, Heidelberg, Germany) of 100 $\mu$l. The reactions were performed in a thermocycler (OmniGene, MWG-Biotech, Ebersberg, Germany) using the following temperature program: Initial denaturing step of 3 min. 94° C., followed by 25 cycles of 94° C. for 1 minute, 48° C. for 1 minute and 72° C. 1 minute.

The reverse primer was synthesized (about 0.2 $\mu$mol) on a Milligen 7500 and purified with RP-HPLC. The biotinylated forward primer was purchased HPLC-purified from Pharmacia Biotech.

Sequences:

Forward primer: 5'd(bio-GTAAAACGACGGCCAGT)3' (SEQ ID NO:6)
Reverse primer: 5'd(GAGATCTCCTAGGGGCC)3' (SEQ ID NO:7)

Step 2

The PCR product was separated from unincorporated primer by ultrafiltration through a 10,000 Da molecular weight cutoff membrane. Ultrafiltration was done using Ultrafree-MC filtration units (Millipore, Eschbom, Germany) according to the protocol of the provider with centrifugation at 8000 rpm for 20 minutes.

25 $\mu$l (10$\mu$g/$\mu$l) streptavidin Dynabeads M-280 with a nominal size of 2.8 $\mu$m (Dynal, Hamburg, Germany) were prepared according to the instructions of the manufacturer and resuspended in 25 $\mu$l of B/W buffer (10 mM Tris-HCl, pH 7.5, 1 M EDTA, 2 M NaCl). This suspension was added to the PCR samples (still in the filtration unit) and the mixture was incubated with gentle shaking for 15 minutes at ambient temperature. The suspension was transferred to a 1.5 ml Eppendorf tube and the supernatant was separated with the aid of a Magnetic Particle Collector, MPC, (Dynal, Hamburg, Germany). After immobilization the double-stranded PCR product was denatured using 20 $\mu$l 8 M urea After removing the urea (containing the non-biotinylated strand) the beads were washed twice with 50 $\mu$l of 0.07 M ammonium citrate solution, pH 8.0 (the supernatant was removed each time using the MPC). To perform the cleavage reaction and recover the biotinylated single stranded PCR product, the beads were resuspended in 25 $\mu$l of 25% $NH_4OH$ suprapur (Merck, Darmstadt, Germany) and incubated at 60° C. for ten minutes. The supernatant was removed and saved, the $NH_4OH$ treatment was repeated once. Both supernatants were dried in a speedvac and resuspended in 2 $\mu$l of ultrapure water (MilliQ UF plus, Millipore, Eschborn, Germany).

Step 3

1 $\mu$l of the resuspended DNA from step 2 was mixed with $0.2 \times 10^{-3}$ U of snake venom phosphodiesterase (Boehringer Mannheim, Germany) and incubated for 20 min. at 37° C. The reaction was mixed with 1 $\mu$l matrix solution (0.7 M 3-hydroxypicolinic acid in 50% acetonitrile, 70 mM ammonium citrate) and directly used for MALDI-TOF-MS analysis.

Step 4

The reaction products were analyzed using MALDI-TOF MS (141 shots, laser power 5) (FIG. 7) according to the procedure described above.

Figure 7:
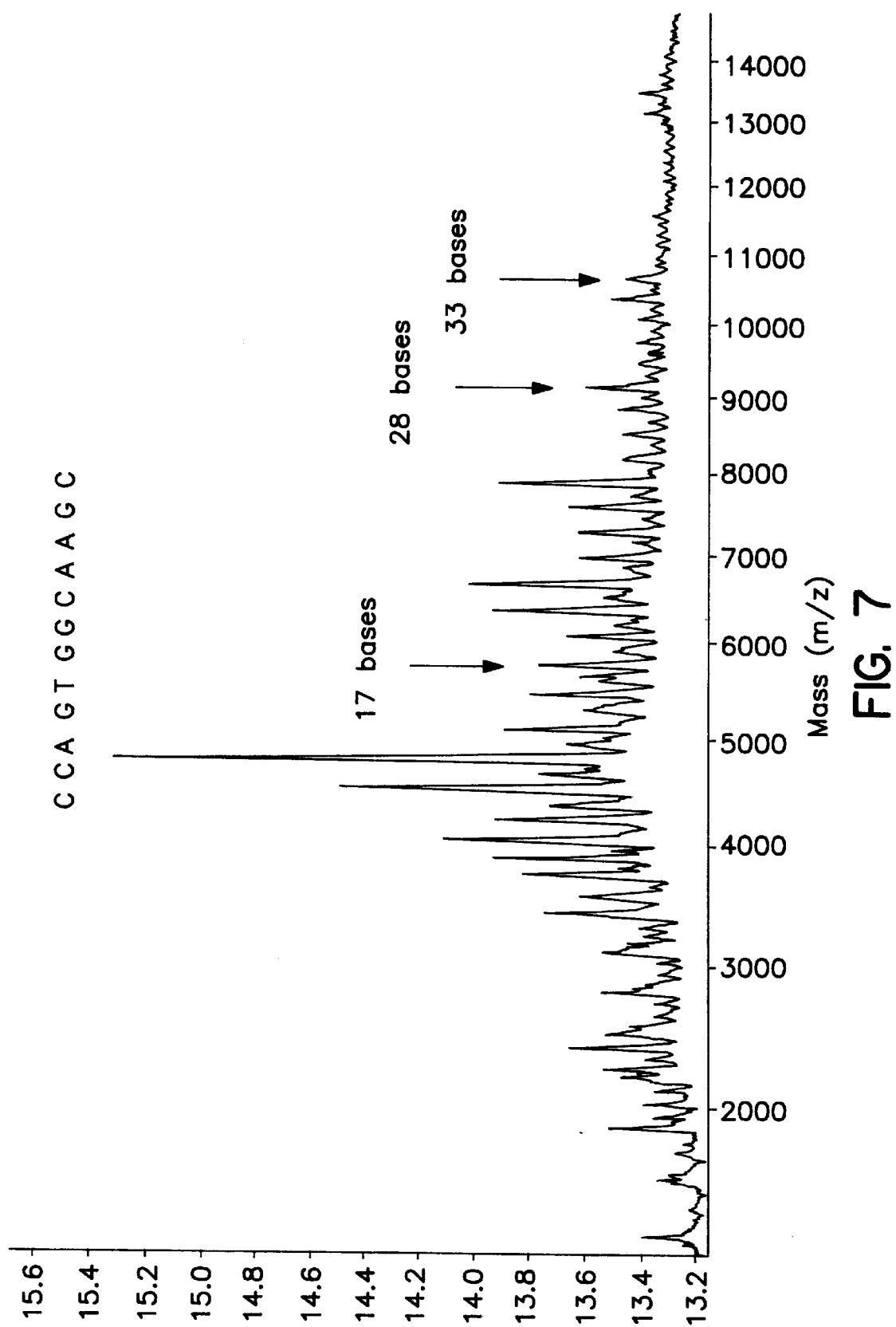
FIG. 7 shows a mass spectrum of an exonucleolytic digest of a 60 mer PCR product.

FIG. 7 shows a spectrum of an exonucleolytic digest of a 60 mer PCR product. The biotinylated PCR product was immobilized on streptavidin Dynabeads and denatured with 8 M urea. The biotinylated single strand was recovered from the beads using treatment with ammonium hydroxide. After lyophilization, the single-stranded 6 mer was digested with snake venom phosphodiesterase. As described in example 4, the spectrum represents a digestion time of 20 minutes at 37° C.

Example 5

MALDI-TOF MS Analysis of an Exonuclease Digestion of Immobilized Oligonucleotides Step 1

400 pmol of the biotinylated 25 mer oligonucleotide were incubated with 2 mg of Dynabeads according to the protocol of the provider in a final volume of 100 $\mu$l.

Step 2

The immobilized oligonucleotide was digested by addition of 3 $\mu$l snake venom phosphodiesterase ($6 \times 10^{-3}$ U) (Boehringer Mannheim, Germany) at room temperature.

Step 3

Aliquots of 20 $\mu$l were taken after digestion for 4, 10, 15, 20 and 25 minutes and were subjected to the same purification procedure as described in Example 2, step 2, supra.

Step 4

The reaction products were analyzed using MALDI-TOF MS according to the procedure described above (FIG. 8).

For the digestion, a 5'-biotinylated oligonucleotide purchased HPLC-purified from Biometra (Göttingen, Germany) was used.

Sequence: 5'd(bio-TACATTCCCAACCGCGTGG CACAAT)'3 (SEQ ID NO:8)

Figure 8:
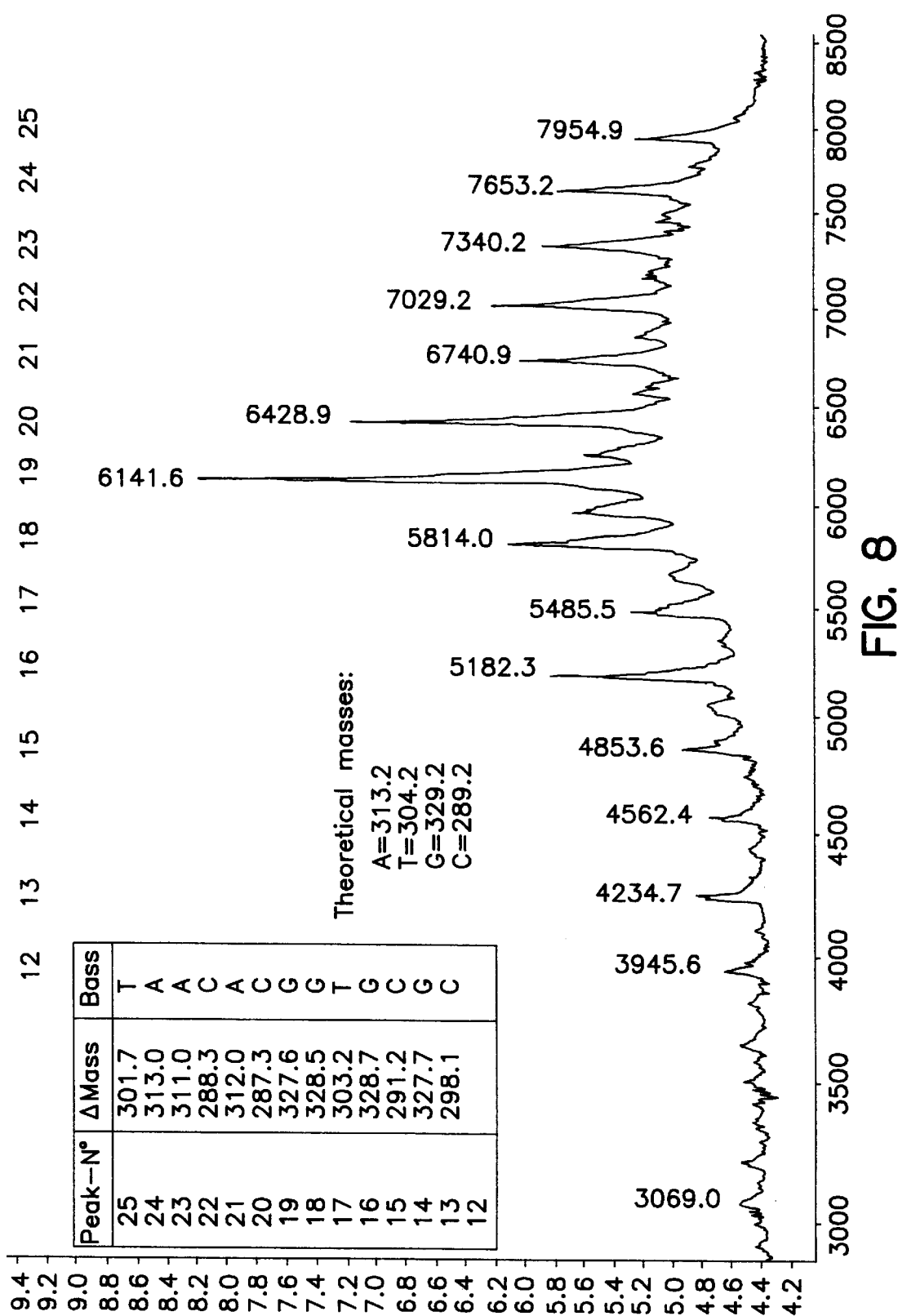
FIG. 8 shows an exonucleolytic digestion of a biotinylated 25 mer immobilized on Dynabeads.

FIG. 8 shows an exonucleolytic digestion of a biotinylated 25 mer immobilized on Dynabeads. After 4 minutes of digestion with snake venom phosphodiesterase the products where purified and removed from the beads, as described above. From this spectrum, the base sequence from base 13 to base 25 can be seen.

Examples 4 and 5 demonstrate that the method described herein can be used for isolation of single-stranded DNA accessible for subsequent enzymatic degradation. Example 4 shows an application where formation of a biotin-streptavidin complex, followed by treatment with ammonium hydroxide, is used to isolate a single strand PCR product for the purpose of digestion with a single-strand-specific exonuclease to determine the nucleotide sequence. This experiment also demonstrates that the recovered biotinylated material remains unmodified and accessible for enzymatic reactions. In example 5, the digestion was carried out while the single-stranded PCR product was still immobilized and the products were recovered using the cleavage method introduced herein.

As can be seen from the Examples, the subject method provides a process for purification and analysis of biotinylated molecules. The inventive method is compatible with mass spectrometric analysis, and with the potential of performing further enzymatic reactions.

In another aspect, the invention provides a kit for analyzing a biotinylated biomolecule. In one embodiment, the kit includes a biotin-binding compound immobilized on a solid support, and an amine. The biotin-binding compound and amine are preferably sealed in separate containers. In preferred embodiments, the kit further includes instructions for dissociating a biotin compound:biotin-binding compound complex with the amine.

The contents of all reference and published patent applications cited throughout this specification are hereby incorporated by reference in their entirety.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for dissociating a biotin compound:biotin-binding compound complex, the method comprising:
contacting the complex with an effective amount of an amine at pH of about 7 to about 14, thereby releasing a biotin compound and a biotin-binding compound, wherein the complex is contacted with an amine at a temperature of about 25° C. to about 100° C.

2. A method for dissociating a biotin compound:biotin-binding compound complex, the method comprising:
contacting the complex with an effective amount of an amine at pH of about 7 to about 14, thereby releasing a biotin compound and a biotin-binding compound, wherein the biotin compound is a biotinylated macromolecule.

3. The method of claim 2, wherein the biotinylated macromolecule is selected from the group consisting of a biotinylated nucleic acid sequence, a biotinylated protein, a biotinylated carbohydrate, and a biotinylated lipid.

4. A method for dissociating a biotin compound:biotin-binding compound complex, the method comprising:
contacting the complex with an effective amount of an amine at pH of about 7 to about 14, thereby releasing a biotin compound and a biotin-binding compound, wherein the biotin-binding compound is selected from the group consisting of avidin, streptavidin, and derivatives thereof.

5. The method of claim 4, wherein the biotin-binding compound is immobilized on a solid support.

6. The method of claim 5, wherein the solid support is a magnetic bead.

7. A method for dissociating a biotin compound:biotin-binding compound complex, the method comprising:
contacting the complex with an effective amount of an amine at pH of about 7 to about 14, thereby releasing a biotin compound and a biotin-binding compound, wherein, after the contacting step, the biotin compound is separated from the biotin-binding compound.

8. The method of claim 7, wherein, afer the separation step, the biotin compound is purified.

9. The method of claim 8, wherein the biotin compound is purified by a method selected from the group consisting of lyophilization, precipitation, crystallization, filtration, dialysis, chromatography and electrophoresis.

10. A method for dissociating a biotin compound:biotin-binding compound complex, the method comprising:
contacting the complex with an effective amount of an amine at pH of about 7 to about 14, thereby releasing a biotin compound and a biotin-binding compound, wherein, prior to the contacting step, the complex is purified.

11. A method for dissociating a biotin compound:biotin-binding compound complex, the method comprising:
contacting the complex with an effective amount of an amine at pH of about 7 to about 14, thereby releasing a biotin compound and a biotin-binding compound, wherein the biotin compound is immobilized on a solid support.

12. A method for dissociating a biotin compound:biotin-binding compound complex, the method comprising:
contacting the complex with an effective amount of an amine at pH of about 7 to about 14, thereby releasing a biotin compound and a biotin-binding compound, wherein, after dissociation of the complex, at least one of the biotin compound and the biotin-binding compound is analyzed by mass spectrometry.

13. A method for dissociating a biotin compound:biotin-binding compound complex, the method comprising:
contacting the complex with an effective amount of an amine at pH of about 7 to about 14, thereby releasing a biotin compound and a biotin-binding compound, wherein, after dissociation of the complex, the biotin-binding compound -retains biotin-binding activity.

14. A method for dissociating a biotin compound:biotin-binding compound complex, the method comprising:
contacting the complex with an effective amount of an amine at pH of about 7 to about 14, thereby releasing a biotin compound and a biotin-binding compound, wherein, after dissociation of the complex, the biotin moiety of the biotin compound remains substantially intact.

15. A method for dissociating a biotin compound:biotin-binding compound complex, the method comprising:
contacting the complex with an effective amount of an amine at pH of about 7 to about 14, thereby releasing a biotin compound and a biotin-binding compound, wherein the amine is ammonia.

16. A method for dissociating a biotin compound:biotin-binding compound complex, the method comprising:
contacting the complex with an effective amount of an amine at pH of about 7 to about 14, thereby releasing a biotin compound and a biotin-binding compound, wherein the amine is a primary amine.

17. A method for dissociating a biotin compound:biotin-binding compound complex, the method comprising:
contacting the complex with an effective amount of an amine at pH of about 7 to about 14, thereby releasing a biotin compound and a biotin-binding compound, wherein the complex is contacted with an amine at a concentration of about 5% to 28%.

18. A method for dissociating a biotin compound:biotin-binding compound complex, the method comprising:

contacting the complex with an effective amount of an amine at pH of about 7 to about 14, thereby releasing a biotin compound and a biotin-binding compound, wherein:

the amine has the formula $NR'_3$ or $N^+R'_4$, in which each R' is independently selected from hydrogen, alkyl, cycloalkyl, alkenyl, alkynyl and aryl.

19. A method for analyzing a biotinylated nucleic acid, comprising:

contacting the biotinylated nucleic acid with a biotin-binding compound, thereby forming a biotinylated nucleic acid:biotin-binding compound complex;

contacting the complex with an effective amount of an amine, under conditions such that a complex is dissociated; thereby releasing a biotinylated nucleic acid and a biotin-binding compound; and analyzing the biotinylated nucleic acid, wherein the amine has the formula $NR'_{30}$ or $N_{30}R'_4$, in which each R' is independently selected from hydrogen, alkyl, cycloalky, alkenyl, alkynyl and aryl, wherein the biotinylated nucleic acid is analyzed by mass spectrometry.

20. A method for analyzing a biotinylated nucleic acid, comprising:

contacting a biotinylated nucleic acid:biotin-binding compound complex with an effective amount of an amine, under conditions such that a complex is dissociated; thereby releasing a biotinylated nucleic acid and a biotin-binding compound; and analyzing the biotinylated nucleic acid by mass spectrometry.

21. The method of claim 20, wherein, after the contacting step, the biotinylated nucleic acid is subjected to an enzymatic reaction.

22. The method of claim 20, wherein: the complex is formed by contacting a biotinylated nucleic acid with a biotin-binding compound to form the biotinylated nucleic acid:biotin-binding compound complex; and before formation of the complex, the biotinylated nucleic acid is subjected to an enzymatic reaction.

23. The method of claim 21, wherein the enzymatic reaction comprises treatment with an enzyme selected from the group consisting of endonucleases and exonucleases.

24. The method of claim 5, wherein, prior to the contacting step, the complex is purified.

25. The method of claim 20, wherein the biotin-binding compourid is immobilized on a solid support.

26. The method of claim 20, wherein the biotinylated nucleic acid is analyzed by mass spectrometry.

27. A method for analyzing a biotinylated nucleic acid, comprising:

contacting the biotinylated nucleic acid with a biotin-binding compound, thereby forming a biotinylated nucleic acid:biotin-binding compound complex;

contacting the complex with an effective amount of an amine, under conditions such that a complex is dissociated; thereby releasing a biotinylated nucleic acid and a biotin-binding compound; and analyzing the biotinylated nucleic acid, wherein the amine has the formula $NR'_3$ or $N_{30}R'_4$, in which each R' is independently selected from hydrogen, alkyl, cycloaky, alkenyl, alkynyl and aryl, wherein, after the contacting step, the biotinylated nucleic acid is subjected to an enzymatic reaction.

28. A method for analyzing a biotinylated nucleic acid, comprising:

contacting the biotinylated nucleic acid with a biotin-binding compound, thereby forming a biotinylated nucleic acid:biotin-binding compound complex;

contacting the complex with an effective amount of an amine, under conditions such that a complex is dissociated; thereby releasing a biotinylated nucleic acid and a biotin-binding compound; and analyzing the biotinylated nucleic acid, wherein the amine has the formula $NR'_3$ or $N_{30}R'_4$, in which each R' is independently selected from hydrogen, alkyl, cycloalky, alkenyl, alkynyl and aryl, wherein: the complex is formed by contacting a biotinylated nucleic acid with a biotin-binding compound to form the biotinylated nucleic acid:biotin-binding compound complex; and before formation of the complex, the biotinylated nucleic acid is subjected to an enzymatic reaction.

29. A method for dissociating a biotin compound:biotin-binding compound complex, the method comprising:

contacting the complex with an effective amount of an amine at pH of about 7 to about 14, thereby releasing a biotin compound and a biotin-binding compound, wherein the complex is contacted with an amine under pressure of about 1 atm to about 200 atm.

30. A method for dissociating a biotin compound:biotin-binding compound complex, the method comprising:

contacting the complex with an effective amount of an amine at pH of about 7 to about 14, thereby releasing a biotin compound and a biotin-binding compound, wherein the complex is contacted with an amine in a sealed reaction vessel.

31. A method for dissociating a biotin compound:biotin-binding compound complex, the method comprising:

contacting the complex with an effective amount of an amine at pH of about 7 to about 14, thereby releasing a biotin compound and a biotin-binding compound, wherein the biotin-binding compound is an anti-biotin antibody.

32. A method for dissociating a biotin compound:biotin-binding compound complex, the method comprising:

contacting the complex with an effective amount of an amine at pH of about 7 to about 14, thereby releasing a biotin compound and a biotin-binding compound, wherein the biotin-binding compound is a fusion protein comprising a domain having biotin-binding activity.

* * * * *

UNITED STATES PATENT AND TRADEMARK OFFICE
CERTIFICATE OF CORRECTION

PATENT NO.    : 6,303,309 B1
DATED         : October 16, 2001
INVENTOR(S)   : Jurinke et al.

It is certified that error appears in the above-identified patent and that said Letters Patent is hereby corrected as shown below:

<u>Title page,</u>
Item [75] Inventors, replace "Dirk Van den Boom, Dreieich," with -- Dirk Van Den Boom, Hamburg, --; and replace "Hubert Koster, Concord, MA (US)" with -- Hubert Koster, La Jolla, CA (US) --.

<u>Column 21,</u>
Starting at line 18, claims 1-2 should read as the following:
   1. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein the complex is contacted with an amine at a temperature of about 25° C to about 100° C.
   2. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein the biotin compound is a biotinylated macromolecule.
Starting at line 36, claim 4 should read as the following:
   4. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein the biotin-binding compound is selected from the group consisting of avidin and streptavidin and deriviatives thereof.
Starting at line 48, claim 7, should read as the following:
   7. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein, after the contacting step, the biotin compound is separated from the biotin-binding compound.
Starting at line 61, claim 10 should read as the following:
   10. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein, prior to the contacting step, the complex is purified.

UNITED STATES PATENT AND TRADEMARK OFFICE
CERTIFICATE OF CORRECTION

PATENT NO. : 6,303,309 B1
DATED : October 16, 2001
INVENTOR(S) : Jurinke et al.

It is certified that error appears in the above-identified patent and that said Letters Patent is hereby corrected as shown below:

Column 22,
Starting at line 17, claims 11-14 should read as the following:
    11. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the biotin compound is immobilized on a solid support.
    12. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein, after dissociation of the complex, at least one of the biotin compound and the biotin-binding compound is analyzed by mass spectrometry.
    13. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein, after dissociation of the complex, the biotin-binding compound retains biotin-binding activity.
    14. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein, after dissociation of the complex, the biotin moiety of the biotin compound remains substantially intact.
Starting at line 47, claims 15-17 should read as the following:
    15. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the amine is ammonia.
    16. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the amine is a primary amine.

UNITED STATES PATENT AND TRADEMARK OFFICE
CERTIFICATE OF CORRECTION

PATENT NO. : 6,303,309 B1
DATED : October 16, 2001
INVENTOR(S) : Jurinke et al.

It is certified that error appears in the above-identified patent and that said Letters Patent is hereby corrected as shown below:

Column 22 (continued),
17. A method for dissociating a biotin compound:biotin-binding compound complex, the method comprising:
  contacting the complex with an effective amount of an amine at a pH of about 7 to about 14, thereby releasing a biotin compound and a biotin-binding compound, wherein the complex is contacted with an amine at a concentration of about 5% to about 28%.
Starting at line 47, to column 23, line 17, claim 18 should read as the following:
  18. A method for dissociating a biotin compound:biotin-binding compound complex, the method comprising:
  contacting the complex with an effective amount of an amine at a pH of about 7 to about 14, thereby releasing a biotin compound and a biotin-binding compound, wherein:
  the amine has the formula $NR'_3$ or $N^+R'_4$, in which each R' is independently selected from hydrogen, alkyl, cycloalkyl, alkenyl, alkynyl and aryl.

Column 23,
Starting at line 8, claim 19 should read as the following:
  19. A method for analyzing a biotinylated nucleic acid, comprising:
  contacting the biotinylated nucleic acid with a biotin-binding compound, thereby forming a biotinylated nucleic acid:biotin-binding compound complex;
  contacting the complex with an effective amount of an amine, under conditions such tat a complex is dissociated; thereby releasing a biotinylated nucleic acid and a biotin-binding compound; and analyzing the biotinylated nucleic acid, wherein the amine has the formula $NR'_3$ or $N^+R'_4$, in which each R' is independently selected from hydrogen, alkyl, cycloalkyl, alkenyl, alkynyl and aryl, wherein the biotinylated nucleic acid is analyzed by mass spectrometry.
Starting at line 45, claim 25 should read as the following:
  25. A method of claim 20, wherein the biotin-binding compound is immobilized on a soild support.

Starting at line 45, to column 24, line 7, claim 27 should read as following:
  27. A method for analyzing a biotinylated nucleic acid, comprising:
  contacting the biotinylated nucleic acid with a biotin-binding compound, thereby forming a biotinylated nucleic acid:biotin-binding compound complex;
  contacting the complex with an effective amount of an amine, under conditions such tat a complex is dissociated; thereby releasing a biotinylated nucleic acid and a biotin-binding compound; and analyzing the biotinylated nucleic acid, wherein the amine has the formula $NR'_3$ or $N^+R'_4$, in which each R' is independently selected from hydrogen, alkyl, cycloalkyl, alkenyl, alkynyl and aryl, wherein, after the contacting step, the biotinylated nucleic acid is subjected to an enzymatic reaction.

UNITED STATES PATENT AND TRADEMARK OFFICE
CERTIFICATE OF CORRECTION

PATENT NO. : 6,303,309 B1
DATED : October 16, 2001
INVENTOR(S) : Jurinke et al.

It is certified that error appears in the above-identified patent and that said Letters Patent is hereby corrected as shown below:

Column 24,
Starting at line 8, claims 28-31 should read as the following:
    28. A method for analyzing a biotinylated nucleic acid, comprising:
    contacting the biotinylated nucleic acid with a biotin-binding compound, thereby forming a biotinylated nucleic acid:biotin-binding compound complex;
    contacting the complex with an effective amount of an amine, under conditions such tat a complex is dissociated; thereby releasing a biotinylated nucleic acid and a biotin-binding compound; and analyzing the biotinylated nucleic acid, wherein the amine has the formula $NR'_3$ or $N^+R'_4$, in which each R' is independently selected from hydrogen, alkyl, cycloalkyl, alkenyl, alkynyl and aryl, wherein: the complex is formed by contacting a biotinylated nucleic acid with a biotin-binding compound to form the biotinylated nucleic acid:biotin-binding compound complex; and
    before formation of the complex, the biotinylated nucleic acid is subjected to an enzymatic reaction.
    29. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the complex is contacted with an amine under pressure of about 1 atm to about 200 atm.
    30. A method for dissociating a biotin compound:biotin-binding compound complex, the method comprising:
    contacting the complex with an effective amount of an amine at a Ph of about 7 to about 14, thereby releasing a biotin compound and a biotin-binding compound, wherein the complex is contacted with an amine in a sealed reaction vessel.
    31. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the biotin-binding compound is an anti-biotin antibody.
Starting at line 47, claim 32 should read as the following:
    32. A method for dissociating a biotin compound:biotin-binding compound complex, the method comprising:

UNITED STATES PATENT AND TRADEMARK OFFICE
CERTIFICATE OF CORRECTION

PATENT NO.    : 6,303,309 B1
DATED         : October 16, 2001
INVENTOR(S)   : Jurinke et al.

It is certified that error appears in the above-identified patent and that said Letters Patent is hereby corrected as shown below:

<u>Column 24 (continued)</u>,
      contacting the complex with an effective amount of an amine at a pH of about 7 to about 14, thereby releasing a biotin compound and a biotin-binding compound, wherein the biotin-binding compound is a fusion protein comprising a domain having biotin-binding activity.

Signed and Sealed this

Fourth Day of June, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.    : 6,303,309 B1
DATED         : October 16, 2001
INVENTOR(S)   : Jurinke et al.

It is certified that error appears in the above-identified patent and that said Letters Patent is hereby corrected as shown below:

Title page,
Item [75] Inventors, replace "Dirk Van den Boom, Dreieich," with -- Dirk Van Den Boom, Hamburg, --; and replace "Hubert Koster, Concord, MA (US)" with -- Hubert Koster, La Jolla, CA (US) --.

Column 21,
Starting at line 18, claims 1-2 should read as the following:
   1. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein the complex is contacted with an amine at a temperature of about 25° C to about 100° C.
   2. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein the biotin compound is a biotinylated macromolecule.
Starting at line 36, claim 4 should read as the following:
   4. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein the biotin-binding compound is selected from the group consisting of avidin and streptavidin and deriviatives thereof.
Starting at line 48, claim 7, should read as the following:
   7. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein, after the contacting step, the biotin compound is separated from the biotin-binding compound.
Starting at line 61, claim 10 should read as the following:
   10. A method for dissociating a biotin compound:biotin-binding compound complex, the method comprising:
      contacting the complex with an effective amount of an amine at a pH of about 7 to about 14, thereby releasing a biotin compound and a biotin-binding compound, wherein, prior to the contacting step, the complex is purified.

UNITED STATES PATENT AND TRADEMARK OFFICE
CERTIFICATE OF CORRECTION

PATENT NO. : 6,303,309 B1
DATED : October 16, 2001
INVENTOR(S) : Jurinke et al.

It is certified that error appears in the above-identified patent and that said Letters Patent is hereby corrected as shown below:

Column 22,
Starting at line 17, claims 11-14 should read as the following:

11. A method for dissociating a biotin compound:biotin-binding compound complex, the method comprising:
contacting the complex with an effective amount of an amine at a pH of about 7 to about 14, thereby releasing a biotin compound and a biotin-binding compound, wherein the biotin compound is immobilized on a solid support.

12. A method for dissociating a biotin compound:biotin-binding compound complex, the method comprising:
contacting the complex with an effective amount of an amine at a pH of about 7 to about 14, thereby releasing a biotin compound and a biotin-binding compound, wherein, after dissociation of the complex, at least one of the biotin compound and the biotin-binding compound is analyzed by mass spectrometry.

13. A method for dissociating a biotin compound:biotin-binding compound complex, the method comprising:
contacting the complex with an effective amount of an amine at a pH of about 7 to about 14, thereby releasing a biotin compound and a biotin-binding compound, wherein, after dissociation of the complex, the biotin-binding compound retains biotin-binding activity.

14. A method for dissociating a biotin compound:biotin-binding compound complex, the method comprising:
contacting the complex with an effective amount of an amine at a pH of about 7 to about 14, thereby releasing a biotin compound and a biotin-binding compound, wherein, after dissociation of the complex, the biotin moiety of the biotin compound remains substantially intact.

Starting at line 47, claims 15-17 should read as the following:

15. A method for dissociating a biotin compound:biotin-binding compound complex, the method comprising:
contacting the complex with an effective amount of an amine at a pH of about 7 to about 14, thereby releasing a biotin compound and a biotin-binding compound, wherein the amine is ammonia.

16. A method for dissociating a biotin compound:biotin-binding compound complex, the method comprising:
contacting the complex with an effective amount of an amine at a pH of about 7 to about 14, thereby releasing a biotin compound and a biotin-binding compound, wherein the amine is a primary amine.

UNITED STATES PATENT AND TRADEMARK OFFICE
CERTIFICATE OF CORRECTION

| | |
|---|---|
| PATENT NO. : 6,303,309 B1 | |
| DATED : October 16, 2001 | |
| INVENTOR(S) : Jurinke et al. | |

It is certified that error appears in the above-identified patent and that said Letters Patent is hereby corrected as shown below:

Column 22 (continued),
17. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the complex is contacted with an amine at a concentration of about 5% to about 28%.
Starting at line 47, to column 23, line 17, claim 18 should read as the following:
    18. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein:
    the amine has the formula $NR'_3$ or $N^+R'_4$, in which each R' is independently selected from hydrogen, alkyl, cycloalkyl, alkenyl, alkynyl and aryl.

Column 23,
Starting at line 8, claim 19 should read as the following:
    19. A method for analyzing a biotinylated nucleic acid, comprising:
    contacting the biotinylated nucleic acid with a biotin-binding compound, thereby forming a biotinylated nucleic acid:biotin-binding compound complex;
    contacting the complex with an effective amount of an amine, under conditions such that a complex is dissociated; thereby releasing a biotinylated nucleic acid and a biotin-binding compound; and analyzing the biotinylated nucleic acid, wherein the amine has the formula $NR'_3$ or $N^+R'_4$, in which each R' is independently selected from hydrogen, alkyl, cycloalkyl, alkenyl, alkynyl and aryl, wherein the biotinylated nucleic acid is analyzed by mass spectrometry.
Starting at line 45, claim 25 should read as the following:
    25. A method of claim 20, wherein the biotin-binding compound is immobilized on a soild support.

Starting at line 45, to column 24, line 7, claim 27 should read as following:
    27. A method for analyzing a biotinylated nucleic acid, comprising:
    contacting the biotinylated nucleic acid with a biotin-binding compound, thereby forming a biotinylated nucleic acid:biotin-binding compound complex;
    contacting the complex with an effective amount of an amine, under conditions such that a complex is dissociated; thereby releasing a biotinylated nucleic acid and a biotin-binding compound; and analyzing the biotinylated nucleic acid, wherein the amine has the formula $NR'_3$ or $N^+R'_4$, in which each R' is independently selected from hydrogen, alkyl, cycloalkyl, alkenyl, alkynyl and aryl, wherein, after the contacting step, the biotinylated nucleic acid is subjected to an enzymatic reaction.

UNITED STATES PATENT AND TRADEMARK OFFICE
CERTIFICATE OF CORRECTION

PATENT NO. : 6,303,309 B1
DATED : October 16, 2001
INVENTOR(S) : Jurinke et al.

It is certified that error appears in the above-identified patent and that said Letters Patent is hereby corrected as shown below:

<u>Column 24,</u>
Starting at line 8, claims 28-31 should read as the following:
    28. A method for analyzing a biotinylated nucleic acid, comprising:
    contacting the biotinylated nucleic acid with a biotin-binding compound, thereby forming a biotinylated nucleic acid:biotin-binding compound complex;
    contacting the complex with an effective amount of an amine, under conditions such that a complex is dissociated; thereby releasing a biotinylated nucleic acid and a biotin-binding compound; and analyzing the biotinylated nucleic acid, wherein the amine has the formula $NR'_3$ or $N^+R'_4$, in which each R' is independently selected from hydrogen, alkyl, cycloalkyl, alkenyl, alkynyl and aryl, wherein: the complex is formed by contacting a biotinylated nucleic acid with a biotin-binding compound to form the biotinylated nucleic acid:biotin-binding compound complex; and
    before formation of the complex, the biotinylated nucleic acid is subjected to an enzymatic reaction.
    29. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the complex is contacted with an amine under pressure of about 1 atm to about 200 atm.
    30. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the complex is contacted with an amine in a sealed reaction vessel.
    31. A method for dissociating a biotin compound:biotin-binding compound complex, the method comprising:
    contacting the complex with an effective amount of an amine at a pH of about 7 to about 14, thereby releasing a biotin compound and a biotin-binding compound, wherein the biotin-binding compound is an anti-biotin antibody.
Starting at line 47, claim 32 should read as the following:
    32. A method for dissociating a biotin compound:biotin-binding compound complex, the method comprising:

UNITED STATES PATENT AND TRADEMARK OFFICE
CERTIFICATE OF CORRECTION

PATENT NO. : 6,303,309 B1
DATED : October 16, 2001
INVENTOR(S) : Jurinke et al.

It is certified that error appears in the above-identified patent and that said Letters Patent is hereby corrected as shown below:

Column 24 (continued),
contacting the complex with an effective amount of an amine at a pH of about 7 to about 14, thereby releasing a biotin compound and a biotin-binding compound, wherein the biotin-binding compound is a fusion protein comprising a domain having biotin-binding activity.

This certificate supersedes certificate of correction issued June 4, 2002.

Signed and Sealed this

Twenty-third Day of July, 2002

Attest:

Attesting Officer

JAMES E. ROGAN
*Director of the United States Patent and Trademark Office*